US009028853B2

(12) United States Patent
Howland

(10) Patent No.: US 9,028,853 B2
(45) Date of Patent: May 12, 2015

(54) PATHOGEN PROTECTION GARMENT WITH BOTH RAPID AND PERSISTENT RECHARGABLE SELF-STERILIZATION

(75) Inventor: Charles A. Howland, Temple, NH (US)

(73) Assignee: Warwick Mills Inc., New Ipswich, NH (US)

(*) Notice: Subject to any disclaimer, the term of this patent is extended or adjusted under 35 U.S.C. 154(b) by 129 days.

(21) Appl. No.: 13/468,295

(22) Filed: May 10, 2012

(65) Prior Publication Data

US 2012/0219609 A1 Aug. 30, 2012

Related U.S. Application Data

(63) Continuation of application No. PCT/US2010/057477, filed on Nov. 19, 2010.

(60) Provisional application No. 61/262,949, filed on Nov. 20, 2009, provisional application No. 61/310,389, filed on Mar. 4, 2010, provisional application No. 61/354,588, filed on Jun. 14, 2010, provisional application No. 61/370,529, filed on Aug. 4, 2010.

(51) Int. Cl.
*A01N 25/34* (2006.01)
*A01N 43/50* (2006.01)
*B05D 3/00* (2006.01)
*C07D 233/72* (2006.01)
*A41D 31/00* (2006.01)

(52) U.S. Cl.
CPC .......... *C07D 233/72* (2013.01); *A41D 31/0083* (2013.01)

(58) Field of Classification Search
None
See application file for complete search history.

(56) References Cited

U.S. PATENT DOCUMENTS

| | | | |
|---|---|---|---|
| 5,665,810 | A | 9/1997 | Patchett et al. |
| 5,882,357 | A | 3/1999 | Sun et al. |
| 5,959,014 | A | 9/1999 | Liebeskind et al. |
| 6,077,319 | A | 6/2000 | Sun et al. |
| 6,770,287 | B1 | 8/2004 | Sun et al. |
| 7,858,539 | B2 | 12/2010 | Li et al. |
| 2001/0055651 | A1 | 12/2001 | Mo et al. |
| 2002/0090872 | A1 | 7/2002 | Li |
| 2003/0159200 | A1 | 8/2003 | Elrod |
| 2005/0229327 | A1 | 10/2005 | Casella et al. |
| 2008/0104738 | A1 | 5/2008 | Conley et al. |
| 2009/0148637 | A1 | 6/2009 | Zhang et al. |
| 2010/0088827 | A1 | 4/2010 | Knott et al. |

FOREIGN PATENT DOCUMENTS

WO 2004044305 A1 5/2004

OTHER PUBLICATIONS

Barnes, K.; Liang, J.; Worley, S.D.; Lee, J.; Broughton, R.M.; Huang, T.S. Modification of Silica Gel, Cellulose, and Polyurethane with a Sterically Hindered N-Halamine Moiety to Produce Antimicrobial Activity. Journal of Applied Polymer Science, vol. 105, 2306-2313, 2007.*
Sun, Y.; Sun, G. Durable and Regenerable Antimicrobial Textile Materials Prepared by a Continuous Grafting Process. Journal of Applied Polymer Science, vol. 84, 1592-1599, 2002.*
PCT Search Report for PCT Application No. PCT/US2010/057477, Aug. 28, 2011, 2 pages.
Sun, Gang—National Textile Center, National Textile Center Annual Report: NTC Project C02-CD06 (formerly C02-E06), Nov. 2003, 6 pages.
Sun, G., Xu X., Bickett J. R., Williams J.F., (2001) "Durable and Regenerable Antimicrobial Finishing of Fabrics with a New Hydantoin Derivative," Ind. Eng. Chem. Res., vol. 40, 1016-1021.
Sun, G., Xu, X., "Durable and Regenerable Antibacterial Finishing of Fabrics: Biocidal Properties," Text. Chem. Color. 1998, 30 (6), 26-30.
Sun, G., Xu, X., "Durable and Regenerable Antibacterial Finishing of Fabrics: Chemical Structures," Text. Chem. Color. 1999, 31 (5), 31-35.
Williams, Jeffrey F. et al., Antimicrobial Functionality of Healthcare textiles: Current needs, Options, and Characterization of N halamine-Based Finishes, RJTA Vo. 10, No. 4, 2006, 12 pages.
PCT Search Report for PCT Appl. No. PCT/US2012/000301, dated Feb. 5, 2013, 3 pages.
Declaration of Dr. Gang Sun under 37 CFR 1.132 made in U.S. Appl. No. 09/596,808, dated Apr. 15, 2003, 10 pages.
Sun, G. et al., "Durable and Regenerable Antibacterial Finishing of Fabrics with a New Hydantoin Derivative", Ind. Eng. Chem. Res., 2001, pp. 1016-1021, vol. 40, No. 4.

* cited by examiner

*Primary Examiner* — Susan Tran
*Assistant Examiner* — Jessica Worsham
(74) *Attorney, Agent, or Firm* — Maine Cernota & Rardin

(57) ABSTRACT

A moisture-permeable glove or other garment protects against user contamination and cross-contamination by providing both rapid and persistent sterilization. Exposure to halogen of inherent NH groups and/or attached hydantoin can form a persistent outer halamine sterilization layer. A second inner halamine layer intercepts any pathogens that penetrate the outer surface. The garment can be single layer, or can include a detachable inner liner. Embodiments are compatible with rapid decontamination using an alcohol-based agent. Some embodiments provide a 180 second 3-log kill rate for at least *S. aureus* ATCC and *E. coli*. Embodiments include a moistening agent to activate the halamine. An anticut/puncture layer and/or a pathogen barrier layer can also be included. The protective layer can include contiguous layers of soft and hard metal flexed to improve flexibility and Moisture Vapor Transport Rate (MVTR). The pathogen barrier can include urethane and/or CNT fibers. The garment MVTR can be greater than 0.2 g/cm$^2$/min.

24 Claims, 19 Drawing Sheets

PATHOGEN PROTECTION GARMENT WITH BOTH RAPID AND PERSISTENT RECHARGABLE SELF-STERILIZATION

RELATED APPLICATIONS

This application is a continuation of PCT Application No. PCT/US2010/057477 filed on Nov. 9, 2010, which claims the benefit of U.S. Provisional Application Nos. 61/262,949, filed Nov. 20, 2009, 61/310,389 filed Mar. 4, 2010, 61/354,588 filed Jun. 14, 2010, and 61/370,529 filed Aug. 4, 2010, all of which are incorporated herein by reference in their entirety for all purposes.

FIELD OF THE INVENTION

The invention relates to protective garments, and more particularly to garments which provide protection from pathogens.

BACKGROUND OF THE INVENTION

Drug-resistant pathogens represent a significant public health problem which can affect individuals at work, at home, and even in the hospital. Methicillin-Resistant *Staphylococcus Aureus* (MRSA), Vancomycin-Resistant *Staphylococcus Aureus* (VRSA), *Clostridium difficile* (*C. difficile*), and other gram negative pathogens are currently circumventing our traditional approaches to pathogen control, and challenging our capacity to innovate new technical solutions.

In Feb. 10, 2010, Reuters reported that the estimated cost of infections acquired at hospitals alone is $8.1 billion. From a study published in *Archives of Internal Medicine* that same day, Reuters reported finds by researchers that pneumonia patients stayed an extra 14 days after surgery, and that more than 11 percent of them died. "That's the tragedy of such cases," said Anup Malani of the University of Chicago, who worked on the study. "In some cases, relatively healthy people check into the hospital for routine surgery. They develop sepsis because of a lapse in infection control, and they can die." The researchers said that 1.7 million healthcare-associated infections are diagnosed every year. Many are due to drug-resistant bacteria, such as Methicillin Resistant *Staphylococcus Aureus* or MRSA, which cost more to treat because only a few drugs can work against them. These infections can also be caught outside hospitals, and some studies show that such community-acquired infections are also on the rise. One estimate from Pfizer Inc. suggested that treating MRSA alone costs $4 billion a year.

One of the ways that drug-resistant pathogens can be spread is by cross-contamination, whereby the pathogens contaminate the skin and/or clothing of an individual, and then are transferred from one individual to another through personal contact. The risk of cross-contamination is especially great in public and institutional settings where workers interact with the general public. Examples include hospital emergency departments, hospital infectious disease care units, general hospital environments, long-term healthcare facilities, correctional facilities, transportation screening (such as TSA transport screening), some athletic facilities, law enforcement, corrections, toll booth attendants, theater ticket takers, and EMT and fire services. Many of these facilities have already suffered serious outbreaks of infection, and know from experience that these pathogens can be difficult to control.

One emerging technology which can be used to combat cross-contamination is iodine-based pre-operative skin wash, which offers better pathogen-kill efficacy than chlorhexidine. However, even with these products, MRSA, VRSA and *C. difficile* remain difficult to control.

Personal protection equipment ("PPE") such as masks and gloves, gowns, and other protective clothing that can be changed and laundered frequently is often used to protect an individual from exposure to dangerous pathogens, for example in a medical environment, or when investigating a toxic biological spill. Other examples include police, prison guards, custodial personnel, security personnel at airports and other secure installations, toll collectors on roadways, and ticket takers at theaters.

In particular, protective disposable gloves are often worn under such conditions. In these approaches, workers must be trained to be diligent in using the gloves and other protective clothing, and to change them frequently. However, this can lead to considerable cost and waste, as well as loss of valuable time as the user is forced to repeatedly stop whatever he or she is doing so as to sterilize or exchange gloves. In practice, a user may be tempted to minimize compliance with required glove-sterilizing and/or glove-changing procedures, or may occasionally forget to sterilize or change gloves, for example due to being absorbed in performing other duties. Unfortunately, in healthcare settings, management has already learned that procedural controls are not enough. People make too many small procedural errors to rely on this approach exclusively. And in many settings, such as toll and ticket takers, frequent changing of gloves is simply not practical.

In addition, frequent changing of protective gloves can cause contamination of the user, due to handling of used contaminated gloves. If the user fails to properly sterilize his or her hands after removal of contaminated gloves, the user can become infected. Since hand sterilization is typically carried out using an alcohol-based substance, protection from such sterilization does not persist from one glove change to the next, so that even a single failure to properly sterilize hands during a change of gloves can lead to dangerous results.

Of course, exchanging gloves does not provide any protection against cross-contamination that might occur between glove changes. Also, because gloves are typically sterilized by applying an alcohol-based product to the outer surfaces of the gloves, and because these sterilizing products evaporate quickly, this approach to glove sterilization does not provide any protection against cross-contamination between sterilizations.

One approach is to sterilize the user's hands between glove changes with a persistent sterilizing cream, such as a hand cream containing Triclosan, which can provide some back-up protection in case the user's hands are not properly sterilized during a subsequent glove change. However, such a cream may interfere with use of the gloves. Also, abrasion by the glove itself can tend to wear the cream away. In addition, this approach provides no relief from accumulation of perspiration and no added protection against cross-contamination of others if the gloves are not sterilized and/or changed with sufficient frequency.

Efforts to avoid cross-contamination could be much more successful if workers could wear gloves, gowns, and/or other protective garments which were self-decontaminating, and therefore did not need to be changed as often as standard protective garments, and/or could continue to provide protection against cross-contamination even if a busy doctor or nurse, for example, occasionally forgot to change his or her gloves between patients. Many personnel from hospitals, transport security, police, corrections, and other public services typically move from one subject to the next within 30-180 seconds. Therefore, for a self-decontaminating fabric to be effective, it must be able to destroy a wide range of pathogens on its outer surface to a 3-log kill level within 30-180 seconds.

A number of self-decontaminating fabrics are currently on the market, utilizing copper, silver, or hydantoin-attached chloramine. However, for these fabrics the 3-log kill rates for vegetative pathogens are in the range of 1-24 hours, and many, if not most, of these current offerings have little or no affect on endospores such as *C. difficile*. Therefore, while these fabrics may be useful for other purposes, they are not effective for cross contamination control.

A number of other self-decontaminating fabric technologies have been under development for many years, and some of them have been commercialized, including silver coatings and other metal compounds, phenols, chitosan and PHMB to name a few. However, none of these fabrics can provide a sufficiently fast kill time, all have declining performance after washing and use, and none are rechargeable.

In addition, pathogen-protecting gloves are typically not permeable to water vapor, and can cause accumulation of sweat during long use, leading to discomfort and skin irritation, and possibly leading to unwanted cultivation of pathogens in sweat persisting on the skin of the user.

Under some conditions, PPE equipment must provide physical protection in addition to protection from pathogens. Examples include gloves worn by a medical worker providing hypodermic injections, gloves worn by an environmentalist exploring sharp-edged wreckage at a toxic biological spill, and gloves worn by a law enforcement officer frisking a suspect who may be carrying a contaminated knife or drug-related syringe. It can be difficult for such gloves or other PPE equipment to provide sufficient physical protection and pathogen protection, while at the same time maintaining flexibility and breathability. If a glove is not sufficiently flexible, it will impede the activities of the wearer. And if a glove is not sufficiently breathable, it will cause discomfort and skin irritation if worn for extended periods.

Note that the teachings herein are applicable to a variety of types of PPE equipment, such as masks and even complete protection suits, and that the term "glove" is used generically herein to refer to all such PPE equipment, except where the context specifically requires a hand-worn glove.

What is needed, therefore, is a self-decontaminating protective garment such as a glove that provides persistent protection against both cross-contamination and user contamination, preferably having a 3-log pathogen kill rate of between 30 and 180 seconds, and which is easily recharged for continued, long-term use, while maintaining flexibility and breathability. For some applications, what is further needed is a physical barrier to pathogen penetration, and/or a physical barrier which resists cuts and punctures.

SUMMARY OF THE INVENTION

One general aspect of the present invention is a moisture-permeable protective garment that provides two distinct modes of protection against user contamination by pathogens and against pathogen cross-contamination. A first, persistent mode of protection is provided by an exposed, outward-facing surface of the garment that is treatable with a halogen such as chlorine so as to form thereon a persistent halogen-based sterilizing layer. In embodiments, a second, rapid mode of protection is provided due to compatibility of the outward-facing surface with repeated sterilization by contact with an alcohol-based agent. In addition, the protective garment includes an inner surface that is treatable with halogen so as to form thereon a persistent halogen-based sterilizing layer, the inner surface being configured so as to intercept pathogens that somehow penetrate the outward-facing surface, thereby providing additional protection against user contamination in case the outward-facing sterilizing layer is breached.

In various embodiments, the treatable inner surface is an inward-facing surface that is maintained in contact with the skin of a user wearing the garment, thereby decontaminating the user's skin if the skin becomes contaminated, for example while the garment is being exchanged or is otherwise not in use. In some embodiments, the garment is formed from a single layer of garment material having a halogen-treatable outward-facing surface and a halogen-treatable inward-facing surface. In other embodiments, the garment includes an inner liner that is worn inside of an outer shell layer of garment material, and the halogen-treatable inner surface is a surface of the liner. In certain embodiments, the inward-facing surface of the inner liner is halogen-treatable, and is held in contact with the skin of the user. In some embodiments, the garment includes more than two physical layers, and/or more than two treatable surfaces.

In various embodiments, the treatable surfaces of the protective garment provide a 3-log pathogen kill rate of between 30 and 180 seconds, thereby enabling protective garments made from the fabric to be effective in inhibiting cross-contamination in public and institutional settings where workers interact with the general public.

In certain embodiments, at least one of the persistent halogen-based sterilizing layers is a bonded chemical layer of chlorine, N-Halamine, and/or chloramine. In certain embodiments, the bonded chemical layer is formed by attachment of halogen directly to NH sites inherent in the garment material, and/or by bonding a layer of hydantoin to the garment material and then formation of chloramine or another halamine by exposing the hydantoin to chlorine, for example chlorine dissolved in a water solution, as is common in household bleach. In various embodiments, the hydantoin is covalently bonded to the garment layer, and in certain embodiments a halogen is covalently bonded to the hydantoin or directly to the garment surface. In some embodiments, the garment provides a Moisture Vapor Transport Rate (MVTR) of greater than 0.2 g/cm$^2$/min.

In various embodiments the outer shell and the inner liner are detachably attached to each other, and are separable for example so as to facilitate recharging with halogen. In certain embodiments the inner liner is attached to the outer shell intermittently, for example some glove outer shells and inner liner layers attached by hook-and-loop attachment at the wrist and/or finger tips.

Periodic disinfection in various embodiments of the outward facing surface by alcohol-based products provides rapid disinfection as needed. A typical requirement is to be able to sterilize the hand contact surface in 15 seconds. This is achievable using most alcohol-based gels, foam and rinse type products. For example, a product having approximately 3 ml of 60% alcohol will provide a kill rate adequate to achieve a 3-4 log reduction in pathogens. The bonded outer halogen-based sterilization layer provides persistent pathogen protection between disinfections, and provides back-up protection in case the user fails to strictly follow an alcohol-based disinfection protocol.

Various embodiments include at least one physical pathogen barrier layer that is impermeable to pathogens. In some of these embodiments, the physical pathogen barrier is permeable to moisture vapor, for example providing a Moisture Vapor Transport Rate (MVTR) of greater than 0.2 g/cm$^2$/min. In certain embodiments, the physical pathogen barrier layer includes a membrane made from a urethane such as TPU, and/or a membrane made from a micro-fiber such as a mat formed from carbon nanotubes (CNT). In some embodiments, the physical pathogen barrier layer is mechanically competent, and includes at least 25% nano-fibers. In other embodiments, the physical pathogen barrier layer has hydrostatic resistance greater than 3 cm of water column and a WVTR of greater than 0.2 mg/cm2/min.

Embodiments of the present invention include a protective layer which provides protection against punctures and cuts. In some of these embodiments, the protective layer includes metal, cermet, and/or ceramic. In certain embodiments, the protective layer includes a layer of contiguous platelets of a soft metal such as zinc deposited on a fabric substrate, and/or a layer of deposited, contiguous platelets of a hard metal such as tungsten steel. In certain of these embodiments, the protective layer is flexed after the metal deposition(s), so as to form cracks and fractures in the platelets, thereby enhancing flexibility and breathability without substantially compromising physical protection. In some embodiments, the protective layer includes components with hardness greater than Rockwell 40 c and/or provides a Moisture Vapor Transport Rate (MVTR) of greater than 0.2 g/cm2/min.

Various embodiments that include a plurality of physical layers combine them such that they are connected only intermittently, and in some of these embodiments at least some of the physical layers are separable, for example so as to facilitate recharging with halogen. Note that the term "physical layer" is used throughout to indicate a mechanically competent layer of garment material such as an outer shell, a protective layer, a physical pathogen barrier membrane, or an inner liner, while terms such as "chemical layer," "halamine layer," and "chloramine layer" are used to refer to a persistent layer of a halogen-based disinfectant bonded to a surface of a physical layer.

Another general aspect of the present invention is an advanced self-decontaminating fabric suitable for the manufacture of gloves, gowns, and other clothing which provides a 3-log pathogen kill rate of between 30 and 180 seconds, thereby enabling protective gloves or other garments made from the fabric to be effective in inhibiting cross-contamination in public and institutional settings where workers interact with the general public.

The self-decontaminating fabric includes a surface-attached halamine such as chloramine as an active biocide. Halamines are easily rechargable systems which are based on exposure to a halogen such as chlorine of siloxane/hydantoin attached to the hydroxyl (OH) groups on cellulose surfaces of the fabric. Halamines have high pathogen kill speeds, and are rechargable in a normal washing process with chlorine bleach. In addition to recharge performance, the siloxane/hydantoin coating is wash-fast, such that there is almost no loss in recharge levels after 20 washings.

In various embodiments, the fabric of the present invention provides enhanced biocide action, as compared to the prior art, due to specific and controlled surface preparation of the fiber surface to maximize available hydroxyl functionality and improved halamine coating on the fiber, which enable surface attachment of halogen of from 6000 to 10,000 ppm. In some embodiments increased availability of free chlorine is provided by control of chloramine disassociation rates when in contact with endospore pathogens.

In embodiments, the fabric of the present invention is engineered to have a very high surface area, so as to enable a high density of chloramine and/or other halamine attachment, and a high degree of interfacial compatibility for intimate contact between pathogens and the fiber surface. Some embodiments include natural cotton fiber, which has a complex surface structure with high surface area to mass ratio. The selection of the cotton fiber type, the design of the yarn and the construction of the woven/knit all have an effect on the achievable chloramine attach density on the finished textile. In various embodiments, the halamine density on the textile surface is at least 10,000 ppm.

In addition, the pre-treatment of the fiber is critical to development of the halamine-attach density on the cotton-fiber surface. Without modification, cotton fiber has a complex group of waxes and pectin-based coatings that obscure the cellulose OH functionality. Various embodiments include controlled surface preparation which maximizes diatomic anion hydroxide (OH) functionality. In some embodiments, the fabric also includes an engineered cotton yarn and textile design that increases the contributing percentage of the fiber area available for endospore contact in the fiber yarn bundle.

The fabric includes a hydrating mechanism which supplies liquid water to the halamine/pathogen interface. The liquid water works with the halamine to improve the destruction kinetics. This enhances the activity of the halamine against certain pathogens, including some spores, which are activated and rendered vulnerable when exposed to water. In some embodiments, the hydrating mechanism includes enhanced OH adsorption functionality, and in other embodiments the hydrating mechanism includes use of bonded moisture scavengers such as silica gel.

Embodiments of the present invention include forms of chloramine and/or other halamine compounds bonded to the surface of the fabric which provide concentrations of free chlorine. Halamine resulting from exposure of amide forms of hydantoin to a halogen are used in some embodiments so as to provide free halogen concentrations of up to approximately 1-2 ppm, while also providing long usage times between halogen recharges. In other embodiments, halamine formed from an imide form of hydantoin such as 1,3-dimethylol-5 5-dimethylhydantoin (also referred to herein as "DMDMH") is used, either alone or in combination with amide and/or other forms of hydantoin.

Imide forms of hydantoin have lower binding energy to halogen ions than amide forms, and can result in up to five times higher levels of free halogen at the textile surface, i.e. up to 10 ppm. Prior to the present invention, imide hydantoin compounds were not used to impart biocidal properties to fabrics, due to their rapid release of halogen and the resulting short usage times between recharging. However, the enhanced fabric surface areas and novel fabric pre-treatments used in embodiments of the present invention enable attached halamine concentrations of up to 6,000 ppm, or even 10,000 ppm, thereby providing usage times of 80 to 400 hours between recharging of the imide hydantoin with halogen.

Table I and Table II below provide pathogen reduction test results for fabric having layers of amide halamine and imide halamine, respectively. The test results were obtained from yarn of size 60/2 pima cotton.

TABLE I

Test Results for Halamine Formed from Amide Hydantoin

| Charge (ppm Cl—) | Bacteria Tested | Bacterial Strain # | Contact Time | Log Reduction |
|---|---|---|---|---|
| 3000 | *S. aureus* | ATCC# 6538 | 5 min | 0.72 |
| 3000 | *S. aureus* | ATCC# 6538 | 15 min | 6.53 |
| 3000 | *S. aureus* | ATCC# 6538 | 30 min | 1.48 |
| 3000 | *E. coli* | ATCC# 25922 | 5 min | 2.07 |
| 5000 | *E. coli* | ATCC# 25922 | 5 min | 2.83 |

TABLE I-continued

Test Results for Halamine Formed from Amide Hydantoin

| Charge (ppm Cl—) | Bacteria Tested | Bacterial Strain # | Contact Time | Log Reduction |
|---|---|---|---|---|
| 3000 | E. coli | ATCC# 25922 | 15 min | 6.11 |
| 5000 | E. coli | ATCC# 25922 | 15 min | 2.01 |
| 3000 | E. coli | ATCC# 25922 | 30 min | 5.96 |
| 3000 | Merck B. subtilis | n/a | 1 hour | 3.72 |
| 3000 | Merck B. subtilis | n/a | 2 hour | 4.78 |
|  | Setlow B. subtilis | BGSC # 1A1 | 1 hour | 0.20 |
| 3000 | Setlow B. subtilis | BGSC # 1A1 | 1 hour | 0.19 |
| 3000 | Setlow B. subtilis | BGSC # 1A1 | 2 hour | 0.25 |
|  | Setlow B. subtilis | BGSC # 1A1 | 4 hour | 0.14 |
| 5000 | Setlow B. subtilis | BGSC # 1A1 | 8 Hour | 0.36 |
| 5000 | Setlow B. subtilis | BGSC # 1A1 | 15.58 Hour | 0.88 |

TABLE II

Test Results for Halamine Formed from Imide Hydantoin

| Charge (ppm Cl—) | Bacteria Tested | Bacterial Strain # | Contact Time | Log Reduction |
|---|---|---|---|---|
| 2010 | S. aureus | ATCC# 6538 | 90 sec | 4.88 |
| 2010 | S. aureus | ATCC# 6538 | 5 min | 5.69 |
| 2010 | Setlow B. subtilis | BGSC # 1A1 | 1 hour | 0.23 |
| 2010 | Setlow B. subtilis | BGSC # 1A1 | 4 hour | 0.32 |
| 4200 | Setlow B. subtilis | BGSC # 1A1 | 6 Hour | 3.51 |

In some embodiments, the fabric of the present invention also provides active halamine biocidal activity on the skin side of the garment, for decontamination of the wearer in case a pathogen penetrates the garment, or skin contact with a pathogen is made before the garment is worn. In some of these embodiments, the skin-side layer of halamine is kept moist by perspiration of the wearer.

Yet another general aspect of the present invention is a pathogen barrier layer formed from carbon nanotubes ("CNT's") that is permeable to moisture while inhibiting the passage of pathogens. Various embodiments thereof comprise a flexible barrier layer assembly comprising a multi-ply non-woven, mechanically competent barrier layer including at least 25% CNT nano-fibers that has hydrostatic resistant greater than 3 cm of water column and a WVTR of greater than 0.2 mg/cm2/min. The process of fiber cleaning, fiber lay-ply-down, and fiber ply adhesive consolidation using Van der Waals forces, hydrogen bonding, and/or London forces results in a barrier layer tensile strength greater than 100 g/25 mm/g/m2.

Still Another general aspect of the present invention is a system of flexible layers consisting of at least one puncture-resistant and cut-resistant protective layer including components with a Rockwell hardness of greater than 40 c, and a mechanically competent, pathogen-resistant barrier layer including at least 25% nano-fibers that has hydrostatic resistance greater than 3 cm of water column and a WVTR of greater than 0.2 mg/cm2/min, the layers being arranged such that during normal use the high-hardness components protect the integrity of the nano-fiber pathogen barrier layer but do not damage the pathogen barrier layer by cutting or self-abrasion.

One general aspect of the present invention is a pathogen protection garment which includes an outer shell of garment material having an exposed, outward-facing first treatable surface, the first treatable surface being treatable with a halogen so as to form thereon a persistent outer halogen-based sterilizing layer, and an unexposed second treatable surface of garment material, the second treatable surface being treatable with halogen so as to form thereon a persistent inner halogen-based sterilizing layer, the second treatable surface being configured so as to intercept pathogens that penetrate the first treatable surface.

In various embodiments, the first treatable surface is compatible with repeated sterilization by contact with an alcohol-based agent. In some embodiments, the pathogen protection garment is a glove. In certain embodiments at least one of the persistent outer halogen-based sterilizing layer and the persistent inner halogen-based sterilizing layer includes a persistent halamine sterilizing layer. And in other embodiments the halamine sterilizing layer has a mass fraction of greater than 100 ppm.

Various embodiments further include a hydrating mechanism adapted for moistening the halamine sterilizing layer. In some of these embodiments the hydrating mechanism includes adsorption of water on a surface of the garment. In other of these embodiments the hydrating mechanism includes absorption of water by a moisture management coating, the moisture management coating including silica gel. And in some of these embodiments the silica gel is attached to a surface of the garment using a cellulose acetate resin.

In certain embodiments the halamine sterilizing layer is of sufficient concentration to provide a maximum 180 second 3-log kill rate, when it is moistened, for at least S. aureus ATCC strain #6538 and E. coli, as determined by an aerosol AATCC Method 100 assessment.

In various embodiments the halamine is chloramine. In some embodiments at least some of the halamine is an amide halamine. In other embodiments at least some of the halamine is an imide halamine. And in some of these embodiments the imide halamine is 1,3-dimethylol-5 5-dimethylhydantoin (also referred to herein as "DMDMH").

In certain embodiments after treatment with halogen the garment is able to provide a 180 second 3-log kill rate during a period of use of at least 80 hours, after which the garment can be recharged with halogen so as to provide another period of use. In other embodiments after treatment with halogen the garment is able to provide a 180 second 3-log kill rate during a period of use of at least 400 hours, after which the garment can be recharged with halogen so as to provide another period of use.

In various embodiments at least one of the first treatable surface and the second treatable surface includes a siloxane/hydantoin compound bonded thereto, the siloxane/hydantoin compound being convertible to a halamine compound when the siloxane/hydantoin compound is exposed to halogen, thereby forming a persistent halamine sterilizing layer. In some of these embodiments, the siloxane/hydantoin compound is covalently bonded to the at least one of the first treatable surface and the second treatable surface.

In certain embodiments at least one of the first treatable surface and the second treatable surface includes N—H groups inherent to underlying garment material thereof, the N—H groups being convertible to halamine N—Cl groups by exposure of the N—H groups to a halogen.

In other embodiments, a treatable surface of the pathogen protection garment includes a hydantoin compound bonded thereto and N—H groups inherent to underlying garment material thereof, and treatment of the treatable surface with a halogen forms a persistent halamine sterilizing layer thereon due both to conversion of the hydantoin to a halamine compound and conversion of the N—H groups to halamine N—Cl groups.

In some embodiments, the second treatable surface is an inward-facing surface of the outer shell of garment material. In other embodiments the second treatable surface is a surface of an inner liner of garment material contained within the outer shell of garment material. In some of these embodiments the second treatable surface is an inward-facing surface of the inner liner. And in some of these embodiments the inner liner is configured so as to maintain the second treatable surface in contact with skin of a user when the pathogen protection garment is worn by the user. In other of these embodiments the inner liner is able to maintain the skin of the user at EN 1500 levels as a result of the contact between the skin of the user and the persistent inner halogen-based sterilizing layer on the inward-facing surface of the inner liner.

In various embodiments the inner liner includes at least one of meta-aramid fiber, mechanically protective fiber, stretch fiber, chlorine resistant PTT stretch polyester, and chlorine resistant PBT stretch polyester.

In certain embodiments the inner liner is detachably attached to the outer shell. In some embodiments the inner liner is detachably attached to the outer shell by hook-and-loop attachment. In other embodiments the pathogen protection garment is a glove, and the inner liner is detachably attached to the outer shell at least at one of a wrist and a fingertip.

In certain embodiments both an inward facing surface and an outward facing surface of the inner liner are treatable with a halogen so as to form thereon persistent inner halamine-based sterilizing layers. In other embodiments the inner liner has a stretch of greater than 40% at 5 pounds-per-inch. And in some embodiments the inner liner is seamless.

In various embodiments the outer shell includes at least one of leather, natural suede, synthetic suede, meta-aramid fabric, para-aramid fabric, chlorine resistant PTT stretch polyester, and chlorine resistant PBT stretch polyester. In some embodiments the outer shell includes a material treated with aniline dye. In other embodiments heat flux through the pathogen protection garment as measured by the ASTM 1868 method is greater than 80 W/K m$^2$.

In certain embodiments the evaporative resistance reference of the pathogen protection garment as measured by the ASTM 1868 method is less than 50 W/pa m$^2$. In other embodiments the garment is constructed in part from a combination yarn that combines N—H functionalized fiber, mechanically protective fiber, and stretch fiber.

In various embodiments the combination yarn is formed by at least one of intimate blending, ply blending, core spinning, and multicolor weaving. In some of these embodiments the N—H functionalized fiber is a meta-aramid fiber, and the mechanically protective fiber is one of fiberglass and LCP Vectran. In other of these embodiments the pathogen garment has a Moisture Vapor Transport Rate (MVTR) of greater than 0.2 g/cm$^2$/min.

Another general aspect of the present invention is a self-decontaminating fabric suitable for manufacture of a garment that is wearable by a wearer so as to inhibit cross-contamination of pathogens between individuals with whom the wearer comes in contact. The self-decontaminating fabric includes a fabric including a first surface and a second surface, a layer of N-Cyclic material such as siloxane/hydantoin attached to the first surface, the layer of N-Cyclic material being chargable with a halogen to form a layer of halamine, the layer of halamine being of sufficient concentration to provide a maximum 180 second 3-log kill rate, when it is moistened, for at least S. aureus ATCC strain #6538 and E. coli, as determined by an aerosol AATCC Method 100 assessment, and a hydrating mechanism adapted for moistening the halamine layer.

In embodiments, at least some of the N-Cyclic material is attached by Van der Waals forces to hydroxyl groups of cellulose included in the first surface. In some embodiments the chloramine layer is able to deliver at least 4,000 ppm of titratable free halogen, and preferably at least 6,000 ppm of titratable free halogen.

In some embodiments the fabric contains cotton fiber. In other embodiments the fabric contains yarns of less than 200 denier (25 s cc) yarn of cotton or other cellulosic fiber.

In certain embodiments the fabric contains a low-twist 80 denier (60/1 cc) yarn. And in some of these embodiments the fabric further includes crimp-balanced construction.

In various embodiments the hydrating mechanism includes adsorption of water on the first surface of the fabric.

In certain embodiments the hydrating mechanism includes absorption of water by a moisture management coating applied to the first surface, the moisture management coating including silica gel. In some of these embodiments the silica gel is attached to the fabric using a cellulose acetate resin. And in some of these embodiments the cellulose acetate resin includes cross linking and/or Van der Waals attachment which improves its wash-durability.

Various embodiments further include a layer of N-Cyclic material such as siloxane/hydantoin attached to the second surface which is chargable with a halogen to form a layer of halamine.

In some embodiments the N-Cyclic material is chloramine. In other embodiments at least some of the N-Cyclic material is an amide halamine.

In various embodiments at least some of the halamine is an imide halamine. And in some of these embodiments the imide halamine is 1,3-dimethylol-5 5-dimethylhydantoin (also referred to herein as "DMDMH").

In certain embodiments after charging with a halogen the fabric is able to provide the 180 second 3-log kill rate during a period of use of at least 80 hours, after which the fabric can be recharged with halogen so as to provide another period of use. And in some of these embodiments after charging with halogen the fabric is able to provide the 180 second 3-log kill rate during a period of use of at least 400 hours, after which the fabric can be recharged with halogen so as to provide another period of use.

Another general aspect of the present invention is a method of producing a self-decontaminating fabric. The method includes providing a fabric, scouring at least a first surface of the fabric and thereby removing surface contaminates, attaching a layer of N-Cyclic material such as siloxane/hydantoin to the first surface of the fabric, the layer of N-Cyclic material being chargable with a halogen to form a layer of halamine, the layer of halamine being of sufficient concentration, when it is moistened, to provide a maximum 180 second 3-log kill rate for at least S. aureus ATCC strain #6538 and E. coli, as determined by an aerosol AATCC Method 100 assessment, providing a hydrating mechanism adapted for moistening the halamine layer, and moistening the halamine layer using the hydrating mechanism.

In embodiments, scouring at least a first surface of the fabric includes scouring the first surface using a multi-stage process which employs cellulase enzyme chemistry.

In some embodiments attaching a layer of N-Cyclic material to the first surface includes forming at least a partially complete garment incorporating the fabric, saturating the garment with N-Cyclic material dissolved in a solvent, removing excess coating from the garment by centrifuging the garment, and flashing the solvent off of the garment by hot air tumble-drying the garment.

In various embodiments attaching a layer of N-Cyclic to the first surface includes using a continuous roll-to-roll process which applies dip, extract, and flash in-line steps to the fabric.

In certain embodiments the N-Cyclic layer is able to deliver at least 4,000 ppm of titratable free halogen, and preferably 6,000 ppm of titratable free halogen.

And in some embodiments providing a hydrating mechanism includes applying a moisture management coating to the first surface, the moisture management coating including silica gel which is attached to the fabric using a cellulose acetate resin, the cellulose acetate resin being attached to the fabric by Van der Walls forces that improve the wash-durability of the attachment.

Yet another general aspect of the present invention is an anti-puncture material suitable for inclusion in a pathogen protection garment, the anti-puncture material comprising a fiber substrate, a substantially contiguous layer of soft metal supported by the fiber substrate, and a substantially contiguous layer of hard metal supported by the fiber substrate, the anti-puncture material being rendered flexible and breathable due to flexing of the anti-puncture material so as to break the contiguous layers of soft and hard metal into abutting segments thereof.

In some embodiments the soft metal comprises at least one of zinc, copper, and aluminum. In other embodiments the hard metal comprises tungsten carbide. In still other embodiments the anti-puncture material has an MVTR greater than 0.10 mg/cm2/min. And in yet other embodiments the anti-puncture material is configured so as to resist penetration by a 28-gage hypodermic needle driven by a force of 400 grams. In certain embodiments the anti-puncture material is configured so as to resist penetration by a 28-gage hypodermic needle driven by a force of 800 grams.

Yet another general aspect of the present invention is a process for manufacturing an anti-puncture material. The process includes thermally spraying or coating a hard layer comprising at least one of metal, cermet, and ceramic onto a fiber substrate, such that the hard layer has a hardness greater than 40 Rc and an MVTR of greater than 0.2 mg/cm2/min., flexing the hard layer and fiber substrate so as to create at least one of seams and cracks between the hard elements, thereby enabling textile-like flexure of the hard layer, and applying an adhesive to the hard layer so as to maintains the hard layer and fiber substrate as a durable assembly.

Still another general aspect of the present invention is a pathogen barrier material suitable for inclusion in a pathogen protection garment. The anti-pathogen barrier material includes a pathogen barrier layer including at least 25% nanofibers, the pathogen barrier layer being resistant to penetration by at least some pathogens, the pathogen barrier layer having hydrostatic resistance greater than 3 cm of water column and a WVTR of greater than 0.2 mg/cm$^2$/min, the pathogen barrier layer having a Moisture Vapor Transport Rate (MVTR) of greater than 0.2 g/cm2/min.

In various embodiments the pathogen barrier material has a tensile strength greater than 100 g/25 mm/g/m2. In other embodiments the nano-fibers comprise at least one of urethane nano-fibers and carbon nanotubes fibers.

Yet another general aspect of the present invention is a protective fabric comprising a plurality of individual layers assembled into a flexible protective system of fibrous layers, including at least one mechanically competent pathogen barrier layer comprising nanofibers, and at least one relatively coarse fibrous protective layer, wherein the coarse fibrous protective layer is coated with hard elements, the plurality of individual layers being configured so as to allow relative motion therebetween without self abrasion.

Another general aspect of the present invention is a flexible assembly or an adhesively controlled assembly which includes an elastomeric layer with high MVTR and elongation greater than 25%, a thin brittle layer bonded to the elastomeric layer, the thin brittle layer comprising a continuous porous layer comprising at least one of metal, cermet, and ceramic, and a woven or knit fibrous substrate bonded to the thin brittle layer, the fibrous substrate being combined with a layer formed of at least 3 plies of thin, non-woven nanofiber mat bonded together, the flexible assembly having in aggregate an MVTR of greater than 0.2 mg/cm$^2$/min and a water column resistance of greater than 3 cm and an aggregate puncture resistance of greater than 400 g to a 28 gauge hypodermic needle.

Yet another general aspect of the present invention is a system of flexible layers comprising at least one puncture-resistant, cut-resistant layer including components with hardness greater than 40 Rc, and a mechanically competent, pathogen resistant layer including at least 25% nanofibers, the system of flexible layers having a hydrostatic resistance greater than 3 cm of water column and a WVTR of greater than 0.2 mg/cm$^2$/min, the layers being arranged so as to cause the puncture-resistant, cut resistant layer to protect the nanofiber layer from external punctures and cuts without abrasively damaging the pathogen resistant layer.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1A:
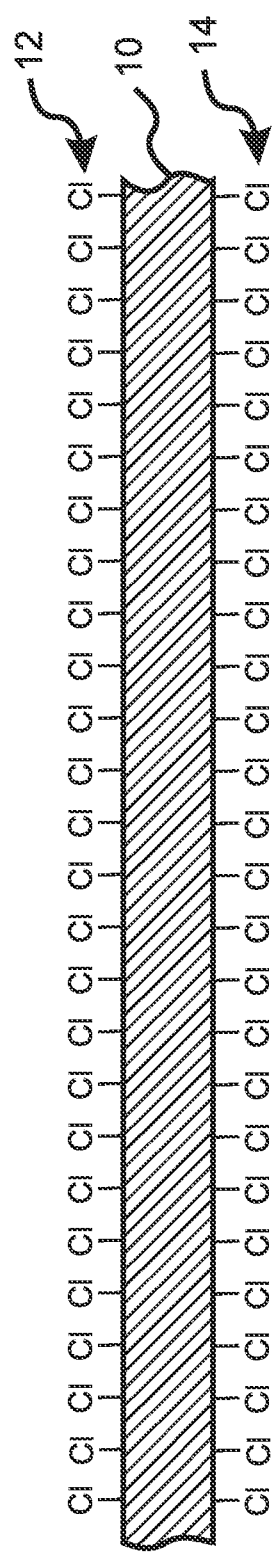
FIG. 1A is a cross-sectional diagram of an embodiment that includes a single physical layer having halamine layers applied to both the inner and the outer surfaces thereof.

With reference to FIG. 1A, one general aspect of the present invention is a protective garment having an outward-facing surface 12 and at least one inner surface 14 that are bondable to and rechargeable with a halogen such as chlorine or bromine so as to form persistent halogen-based sterilizing layers thereupon, such as layers of N-halamine or chloramine. The outward-facing surface 12 is also compatible with disinfection by alcohol-based sterilizing agents, thereby providing an additional, rapid mode of protection against contamination of the user and cross-contamination of others, for example cross-contamination between a plurality of patients being assisted by a health care worker wearing a glove of the present invention.

In embodiments, periodic disinfection by alcohol-based sterilizing agents provides rapid disinfection of the outward-facing surface 12 as needed. A typical requirement is to be able to sterilize the outward-facing surface in 15 seconds. This is achievable using most alcohol-based gels, foams, and rinse type agents. For example, a sterilizing agent having approximately 3 ml of 60% alcohol will provide a kill rate adequate to achieve a 3-4 log reduction in pathogens after 15 seconds of exposure. Outward-facing surfaces of embodiments of the present invention are compatible with long-term exposure to propanol and ethanol materials. This enables rapid disinfection as needed, for example between patients, using an alcohol-based compound.

The outward-facing halogen-based sterilizing layer provides persistent pathogen protection between alcohol product disinfections, and provides back-up protection in case the user fails to strictly follow an alcohol-based disinfection protocol. Use of these two distinct and separate methods for decontamination also discourages the development of disinfection-resistant strains of pathogen. In addition, stitching and seam areas can be difficult to sterilize using only alcohol-based liquid, gels, and/or foams, and the presence of the persistent halogen-based sterilizing layer 12 in these areas can help to ensure control of pathogens over the entire outer surface of the garment.

The persistent halogen-based sterilizing layer formed on the inner surface 14 provides additional protection for the user of the garment in case the outer halogen-based sterilizing layer is breached. In embodiments, the inner halogen-based sterilizing layer 14 is maintained in contact with the skin of a wearer, thereby providing disinfection in case the wearer's skin becomes contaminated, for example during an exchange of gloves or when the glove or other protective garment is temporarily removed so as to recharge the persistent halogen-based sterilizing layers.

Note that the present invention is applicable to many different types of protective garment, such as gloves, masks and even complete protection suits, and that the term "glove" is used herein generically to refer to all such PPE equipment, except where the context specifically requires a hand-worn glove.

Figure 1B:
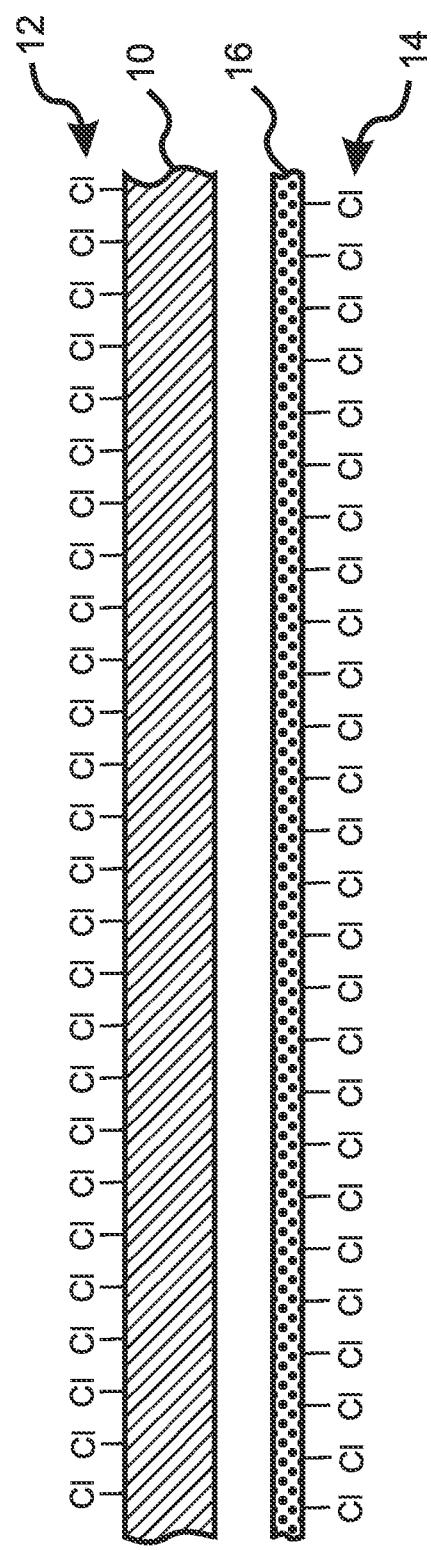
FIG. 1B is a cross-sectional diagram of an embodiment that includes an outer shell layer and an inner liner, the outer shell layer having an outer halamine formed on its outward-facing surface, and the inner liner having an inner layer of halamine formed on its inward-facing surface.

FIG. 1A illustrates an embodiment in which the garment is formed from a single physical layer of garment material 10, and the inner 14 and outer 12 halogen-based sterilizing layers are bonded respectively to the inner and outer surfaces of the single physical layer 10 of garment material. With reference to FIG. 1B, in other embodiments the inner halogen-based sterilizing layer 14 is bonded to a surface of an inner liner 16 worn within an outer shell 10. In the embodiment of FIG. 1B, the inner halogen-based sterilizing layer 14 is bonded to an inward-facing surface of an inner liner 16. Some embodiments include more than two halogen-based sterilizing layers and/or more than two physical layers.

Figure 2B:
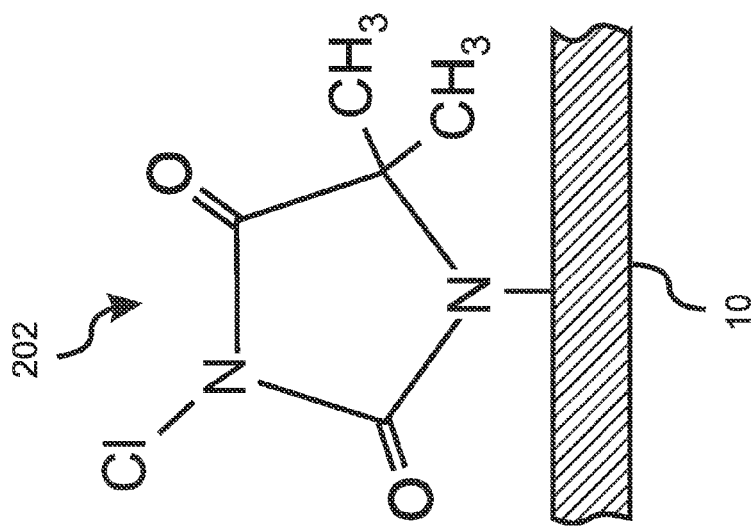
FIG. 2B is a functional diagram indicating the chemical structure of a chloramine compound formed by exposure of the hydantoin compound of FIG. 2A to chlorine.
Figure 2A:
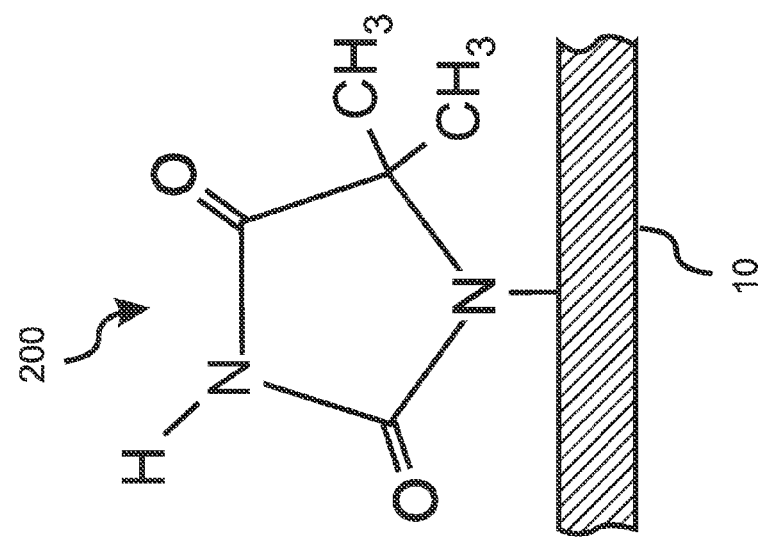
FIG. 2A is a functional diagram indicating the chemical structure of a hydantoin compound attached to a garment layer surface.
Figure 2C:
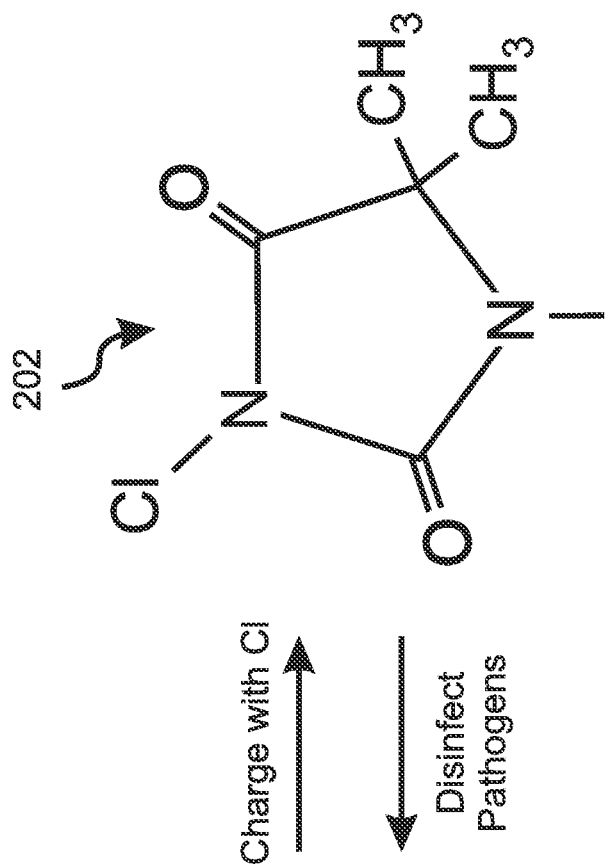
FIG. 2C is a functional diagram indicating a reversible transformation between hydantoin and chloramine as hydantoin is charged with chlorine to become chloramine and then chloramine undergoes a disinfecting reaction with a pathogen to become hydantoin.
Figure 2C:
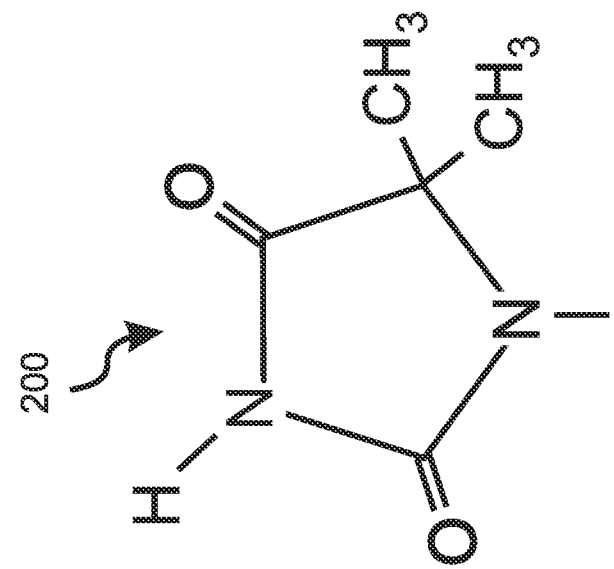

With reference to FIG. 2A, FIG. 2B, and FIG. 2C, in various embodiments, at least one of the halogen-based sterilizing layers includes a halamine such as chloramine 202 formed by bonding a hydantoin compound 200 to a physical layer 100 of the garment and exposing the hydantoin to chlorine. In similar embodiments, the hydantoin is exposed to another halogen, such as bromine. In some embodiments, the hydantoin compound 200 is covalently bonded to the physical layer 100. The hydantoin compound 200 can then be reacted with a chlorine solution so as to form a disinfecting halamine compound 202. Over time, and/or as the halamine compound reacts with pathogens, it reverts to hydantoin 200, and can be re-treated, or "recharged" as needed by re-exposure to chlorine, for example chlorine dissolved in a water solution, as is provided for example by common household bleach. In certain embodiments, the halamine 202 has a mass fraction of greater than 100 ppm. The re-charging process is significantly enhanced by physical agitation during the exposure, so as to increase penetration and permeation of the hydantoin compound layer 200 by the chlorine solution. The charging time under these conditions is consistent with the typical wash cycle in a domestic washing machine.

Figure 3A:
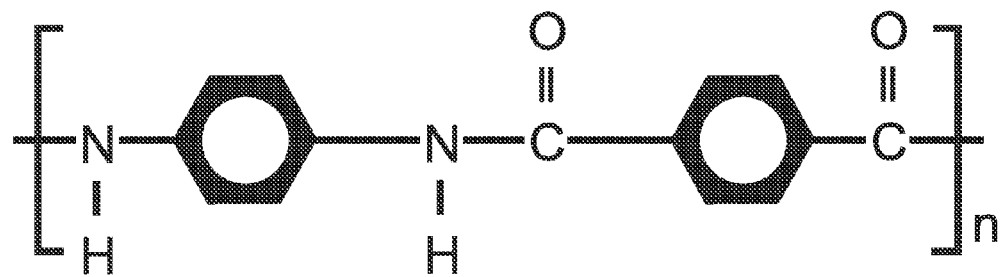
FIG. 3A is a diagram of the chemical structure of a meta-aramid polymer having inherent N—H groups, illustrated before exposure to chlorine.
Figure 3B:
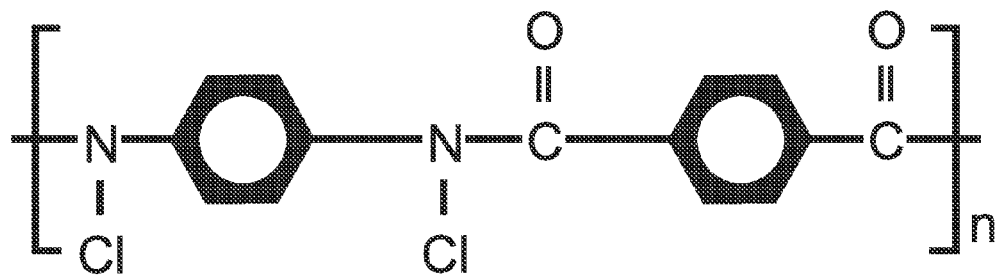
FIG. 3B is a diagram of the meta-aramid polymer of FIG. 3A after exposure to chlorine, wherein the N—H groups have been replaced by N—Cl chloramine groups.

With reference to FIG. 3A and FIG. 3B, in some embodiments at least one of the chlorine-based sterilizing layers is formed by exposing a layer of meta-aramid fabric 300 to a chlorine solution, thereby bonding chlorine 302 directly to the N—H groups that are inherent to the structure of meta-aramid 300.

Halamine Layer Formation

Figure 3C:
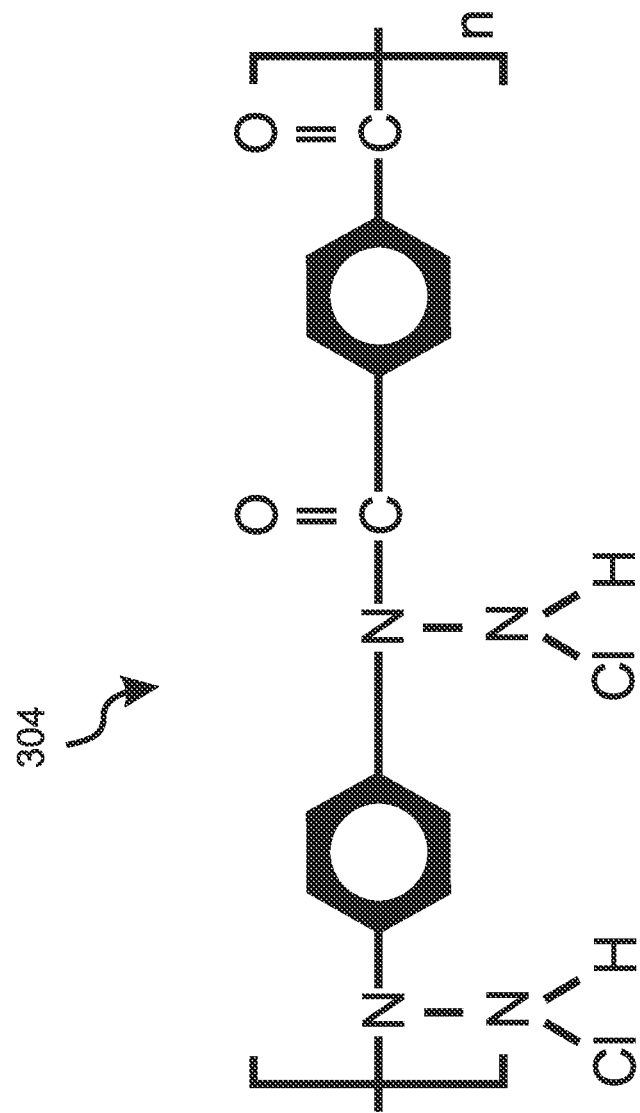
FIG. 3C is a diagram of the meta-aramid polymer of FIG. 3A after exposure to an aqueous $NH_2Cl$ chloramine solution, wherein the N—H groups have been replaced by N—NHCl chloramine groups.

Embodiments of the present invention use either or both of two methods for formation of halamine chemical layers on physical layer surfaces of the protective glove or other PPE. With reference to FIG. 3A, FIG. 3B, and FIG. 3C, one method is the bonding of a halogen atom such as a bromine or a chlorine atom 302 or of a halogen group (e.g. $NH_2Cl$) 304 to an NH group included in the polymer backbone of a synthetic fiber such as meta-aramid 300.

With reference to FIG. 2A and FIG. 2B, the second method for formation of halogen-based chemical layers on physical layer surfaces of the present invention is the attachment of hydantoin functional groups 200 to a fiber surface of the PPE, followed by exposure of the hydantoin to a halogen so as to form N-chloramine 202. In some of these embodiments, the hydantoin is applied to the garment material by a controlled deposition and infrared curing method. And in some embodiments the attachment is covalent. Examples of methods for attaching hydantoin compounds to fabrics and charging the hydantoin compounds with a halogen for anti-pathogen activation can be found in the following journal articles, incorporated herein by reference in their entireties for all purposes: Sun, G., Xu X., Bickett J. R., Williams J. F., (2001) "Durable and Regenerable Antimicrobial Finishing of Fabrics with a New Hydantoin Derivative," *Ind. Eng. Chem. Res.*, Vol. 40, 1016-1021; Sun, G., Xu, X., "Durable and Regenerable Antibacterial Finishing of Fabrics: Biocidal Properties," *Text. Chem. Color.* 1998, 30 (6), 26-30; and Sun, G., Xu, X., "Durable and Regenerable Antibacterial Finishing of Fabrics: Chemical Structures," *Text. Chem. Color.* 1999, 31 (5), 31-35.

Various embodiments of the present invention include meta-aramid 300 as a fiber in one or more physical layers. Meta-aramid 300 has an NH group as part of its polymer structure and has good surface attachment behavior for hydantoin. Meta-aramid is compatible with a number of fabric formation processes, including knitting, weaving, non-woven layed, and needled webs.

Good charge-recharge halogen solution flow is included in some embodiments of the present invention, so as to enhance halogen charging of the nitrogen groups on fiber surfaces. In certain embodiments where yarns are used in knitting and weaving, small denier is used instead of large denier, because halogen recharging solutions migrate more rapidly into small filament fiber bundles than into large filament fiber bundles.

The chloramine content of a chloramine layer 12, 14 is proportional to the area and the density of NH groups on the fiber surface of the physical layer 10 to which the halogen solution is applied so as to form the chloramine layer 12, 14. Therefore, some embodiments attach hydantoin 200 to a surface of a physical layer made from meta-aramid 300 or from a similar garment material in which N—H groups are inherent, so as to form chloramine both from the hydantoin 200 and from the N—H groups inherent to the physical layer 300.

Outer Shell

It will be understood that the term "outer shell" is used herein to refer to the outermost physical layer of the garment. In embodiments where the garment includes only one physical layer, the one physical layer is sometimes referred to as the "shell" or the "outer shell." For example, FIG. 1A illustrates a cross-section of a portion of a protective garment of the present invention in an embodiment that includes only a single physical layer or "outer shell" of Nomex (a meta-aramid) 10 that is coated on both its outer 12 and inner 14 surfaces with layers of a hydantoin compound 200 that have been exposed to a halogen solution such as household bleach, so as to form layers thereon 12, 14 of pathogen-inhibiting chloramine. Similar embodiments include polyester fiber.

FIG. 1B illustrates a cross section of an embodiment that includes an outer shell physical layer 10 with an outward-facing chloramine layer 12 formed thereon, and an inner liner physical layer 16 having an inward-facing chloramine layer 14 formed thereon.

In some embodiments, the outer shell 10 includes natural leather. The basic fibrous material in natural leather is collagen, and this material has adequate alcohol compatibility and provides good comfort. In other embodiments the outer shell includes synthetic materials such as polyester fiber or Nomex, which are also compatible with exposure to alcohol-based sterilizing agents.

In addition to alcohol compatibility, the outer shell 10 in various embodiments has limited liquid permeability, so as to inhibit penetration of applied alcohol-based sterilizing agents to the inner liner 16 (if present) and/or to the skin of the wearer. Typical high-quality, full-grain glove leathers of cow, pig, sheep, goat, deer, and kangaroo are all compatible with this requirement. In some embodiments, contact absorption rates for a typical alcohol-based sterilizing gel such as Purell™ are less than 0.05 ml/cm²/min, causing them to be fully compatible with typical liquid, gel, and foam skin hygiene products. In various hand-worn glove embodiments, the outer shell palm, fourchette, and back of the glove are all fabricated from materials that provide this low level of porosity.

For some embodiments that include full-grain natural leather in the outer shell 10, the leather is finished by treating it with aniline dye. There is very good attachment between aniline and collagen, and between aniline and hydantoin 200, and treatment of leather in the outer shell 10 with aniline dye limits saturation of the leather core and improves the drying time after exposure to a halogen solution for chloramine recharging. Because the leather core is not saturated, the leather outer shell 10 material can sustain more recharge cycles without shrinkage or flexibility issues.

Certain embodiments include synthetic and/or natural suede in at least part of the outer shell 10. Increased hydantoin 200 attachment and higher charge levels of chloramines 202 can be achieved with suede materials as a result of their more porous structures. However, suede outer shell materials saturate with liquid and gel sterilizing agents more quickly than full-grain leathers. The typical process of using liquid or gel alcohol preparations to sterilize a synthetic or natural suede tends to saturate the suede at the point of application and to inhibit full and consistent recharging of the outer shell 10 later with a halogen. Use of a foam-based alcohol preparation avoids this problem, since the use of foam limits the saturation of the alcohol at the point of application, and facilitates uniform application of the alcohol.

In certain embodiments, the outer shell 10 includes thermal and moisture management characteristics that enhance the comfort of the user and improve skin hygiene by limiting the colonization of pathogens in perspiration on the skin surface. In addition, lower moisture levels inside the garment help to maintain good skin tone and reduce chapping and cracking of the skin. In various embodiments, the moisture permeability and thermal performance of the outer shell material 10, as measured by the ASTM 1868 method, include a heat flux through the outer shell material of greater than 80 W/K $m^2$, and in some embodiments greater than or equal to 100 W/K $m^2$. Certain embodiments include an outer shell material 10 with an evaporative resistance of less than 50 W/pa $m^2$.

In some embodiments where the garment is a hand-worn glove, the outer shell 10 is made of a synthetic suede or glove leather on the palm and fingers, and of Meta aramid with LCP and chlorine resistant PTT or PBT stretch polyester on the back. All of the materials of the outer shell 10 in these embodiments are compatible with ethanol and propanol sterilization materials, including gels, foams, and rinses.

In various embodiments, the protective garment is capable of being sterilized before use and after assembly, so as to ensure a pathogen-free starting point for the materials. Both textiles and leather can be sterilized using agents such as the gas ethylene oxide (EtO) or industrial laundry chlorine solutions of concentration 100-400 ppm. These are typical processes used for sterilizing fragile materials that cannot tolerate high temperatures. For embodiments that require recharging of hydantoin 200 by a halogen solution, the garment layer(s) is/are compatible with these agents. In other embodiments, halogen gas and/or halogen dioxide gas can be used to charge the hydantoin surfaces 200 and to ensure disinfection of the PPE garment.

Inner Liner

FIG. 1B illustrates a cross-section of a protective garment of the present invention in an embodiment that includes both an outer shell 10 of meta-aramid, and an inner liner 16. The inherent NH-groups on the outward-facing surface of the outer shell 10 of meta-aramid have been charged with a halogen, and in addition the outward-facing surface 12 has been coated with a layer of a hydantoin compound and charged with a halogen so as to form a layer of chloramine 202 therefrom.

In addition, a removable Tricot inner liner 16 is included, which is made of chlorine-resistant PTT or PBT stretch polyester coated with hydantoin 200 on its inward-facing surface 14, the hydantoin being charged with a halogen to form a chemical layer of chloramine 14. The inner liner 16 is elastic, and is configured to maintain close contact between the inner layer of chloramine 14 and the skin of a wearer, so as to provide additional protection from contamination, and so as to decontaminate the skin of the wearer in case contamination does occur.

In some embodiments that include an inner liner 16, contact between the inner chloramine layer 14 and the user's skin is maximized in two ways. First, the yarn size of the inner liner 16 is kept small, so as to maximize the number of contact points per unit area. Second, the yarn density is selected to be as high as possible. Yarn density in some of these embodiments is balanced with charging requirements and other factors in the design of the PPE. Some of these embodiments include textiles with Fraser Perm values greater than 200 and less than 350 $ft^3/ft^2$/min. In some glove embodiments, the density and mass-per-unit-area of a liner is balanced with the thickness and bulk of the liner. In various of these embodiments the inner liner has a mass of between 1.0 and 4 $oz/yd^2$ and yarn size between 70 denier and 210 denier. Felting of the inner surface is also included in some embodiments because the felting process increases the contact surface with the skin of the user.

The sterilization of skin can be tested using TFM, EN 1499 and 1500 methods. These test methods measure the effectiveness of a candidate sterilization method against a standard sterilization method using a 3 ml wash of propan-2-ol 60%. These methods show that the more intimate the contact between the disinfecting material and the skin, the more rapid and complete is the sterilization process. Embodiments of the present invention include a high-drape inner liner 16. The measurement of drape can be based on conformability of the textile, and can be measured by KES methods or by ASTM 4032 circular bending. Some embodiments use inner liners 16 with stretch wovens and/or knits. Knits excel in drape and are therefore used in various embodiments. In certain embodiments, contact management is enhanced by the use of stretch fiber in the liner system 16. If the inner liner has stretch, it can be patterned to cling tightly to the skin. This maximizes the skin contact. Stretch is generally measured at a load as percentage elongation. In some embodiments, the inner liner 16 includes a stretch of greater than 40% at 5 pounds-per-inch.

Various embodiments of the present invention include a liner 16 that includes textiles of less than 0.015" thickness so as to provide a smooth, tight fit without excessive bulk. In some of these embodiments, seams are kept to a minimum, and/or are designed to lie flat and provide continuous contact with the skin. Certain embodiments use knit-to-shape materials, for example in continuous string-knit gloves, which can be used to produce a smooth, seamless, tight fitting PPE glove inner liner 16.

Certain embodiments comprise a yarn that is a combination of meta-aramid N—H functionalized fiber 300, mechanically protective fiber, and stretch fiber, the combined yarn being formed by intimate blending, ply blending, core spinning, and/or multicolor weaving methods. In various embodiments, these combination yarns provide good chloramine attachment density 202, charge-recharge halogen compatibility, charge-recharge halogen solution permeability, high drape, low bulk, good stretch for fit, and good mechanical protection.

For mechanical protection against both cut and abrasion, in some embodiments the inner liner 106 includes fiber with enhanced cut resistance and tenacity greater than 10 gpd. In some of these embodiments, the cut and abrasion fibers include fiberglass and/or LCP Vectran, which provide durable hydantoin attachment 200.

The inner liner 16 in the embodiment of FIG. 1B is removable from the outer shell 10, so as to facilitate recharging of the chloramine 202. In some glove embodiments, the inner liner 16 is removably attached to the outer shell 10 by hook-and-loop attachment at the cuff, and/or at the fingertips. Typically, both physical layers 10, 16 are recharged with a halogen by being separated and agitated while submerged in a weak solution of approximately 200 ppm hypochlorite, such as is provided by a typical household washing machine containing typical household bleach. The agitation helps to move the charging solution through the filament bundles of the physical layers 10, 16.

Self-Decontaminating Fabric

Another general aspect of the present invention is a self-decontaminating fabric which is suitable for the manufacture of gloves, gowns, and other outer clothing which can inhibit cross-contamination of pathogens between individuals with whom the wearer comes in contact. The fabric provides a 3-log pathogen kill rate of between 30 and 180 seconds on its outer surface, thereby enabling garments made from the fabric to be effective in inhibiting cross-contamination in public and institutional settings where workers interact with the general public. In some embodiments the fabric can also decontaminate the wearer, due to skin contact with the inner surface of the fabric.

The self-decontaminating fabric includes a surface-attached halamine such as chloramine as an active biocide. Halamines are easily rechargable systems which are based on exposure to a halogen of siloxane/hydantoin attached to the hydroxyl (OH) groups on cellulose surfaces of the fabric. Halamines have a high pathogen kill speed, and are rechargable by exposure to chlorine bleach in a normal washing process.

The American Association of Textile Coaters and Colorists (AATCC) 100 method is used as the benchmark for pathogen destruction on textile. For simplicity, this test method applies the pathogen challenge from broth, and the kill time is measured under moist sample conditions. The inventors have developed aerosol dispensing methods for pathogens which deposit a controlled challenge on a textile. This allows more accurate simulation of cross-contamination on a moisture-limited textile surface.

Figure 4:
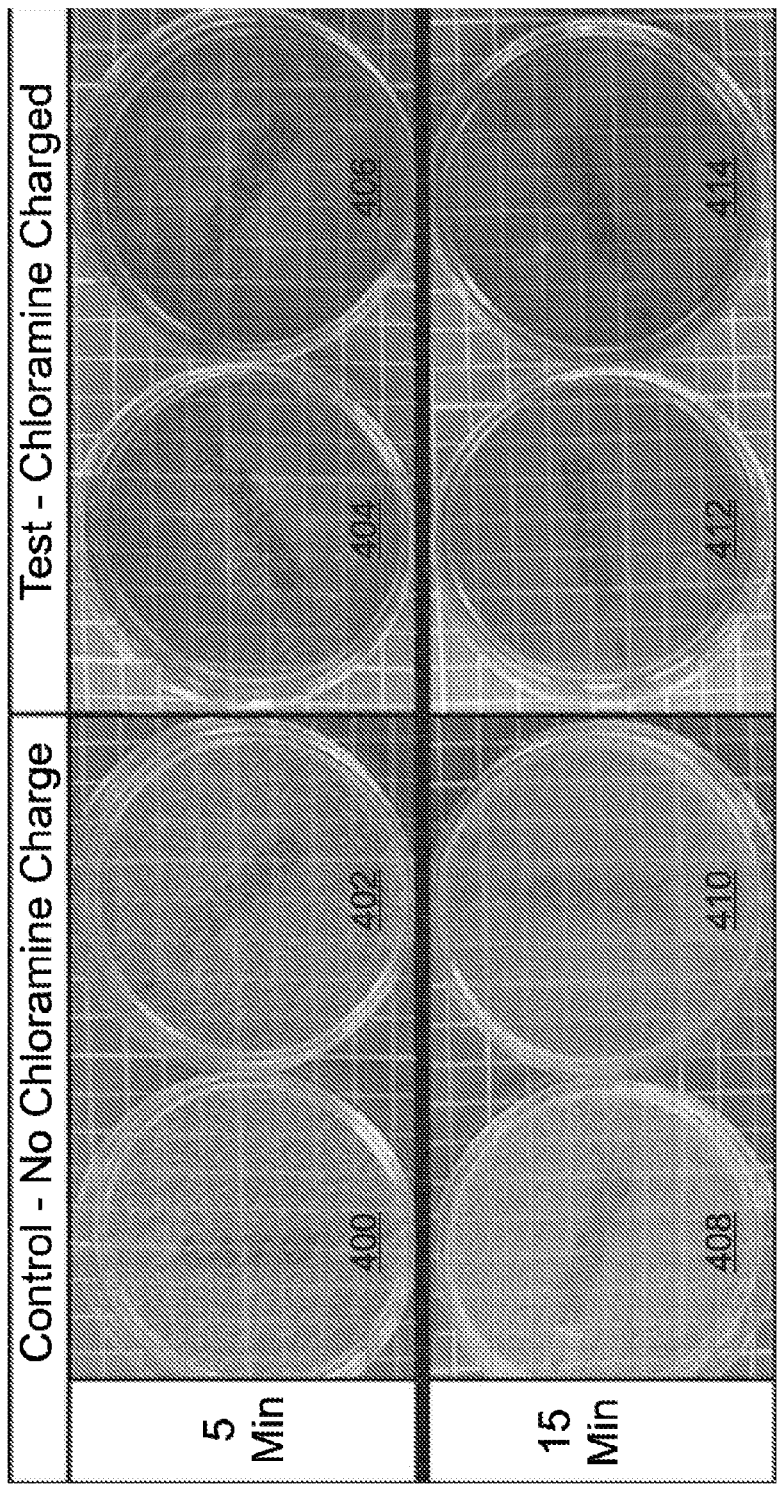
FIG. 4 shows the results of an aerosol AATCC Method 100 assessment of antibacterial finishes on cotton fabric with titrated free chlorine at 3000 ppm.
Figure 5A:
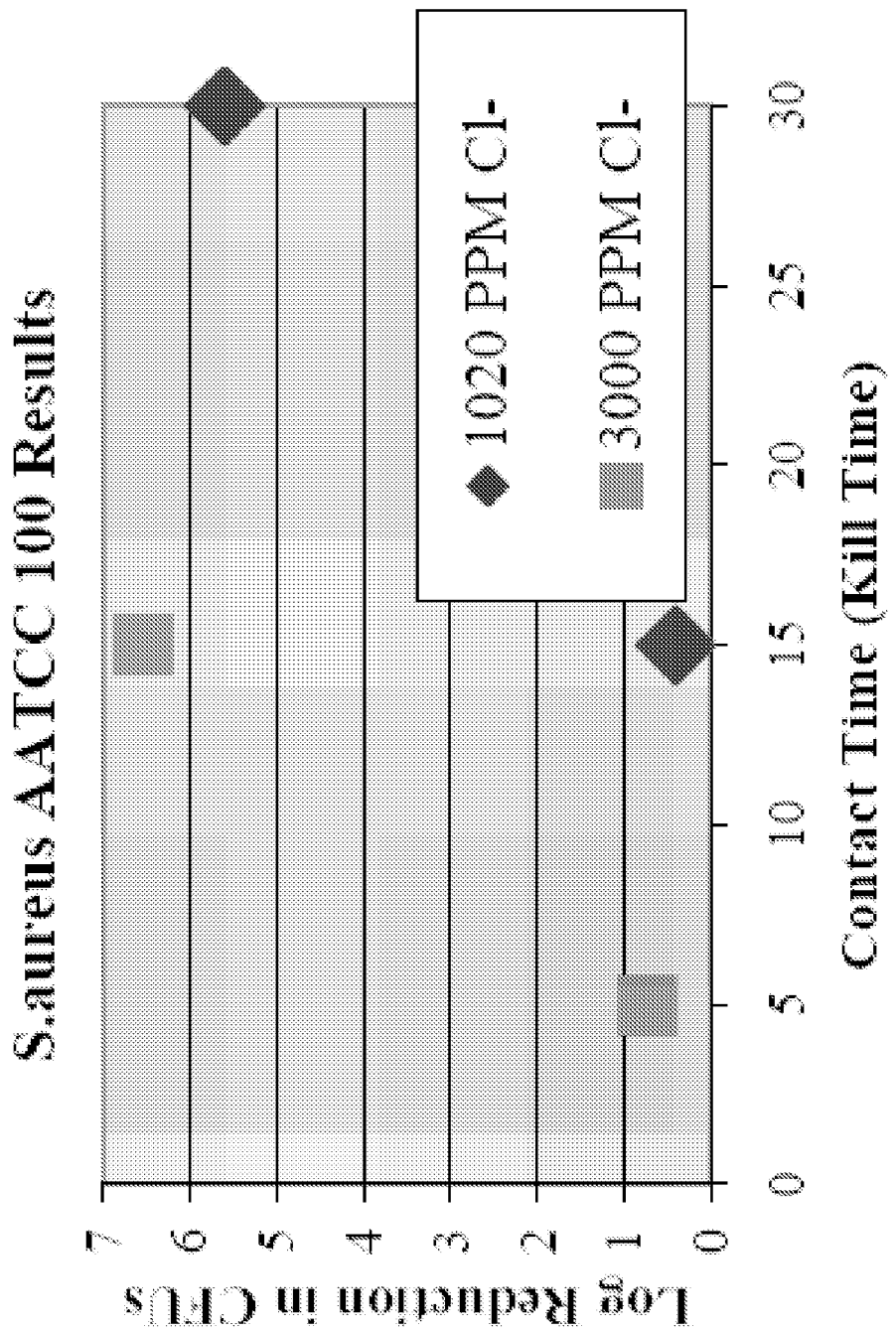
FIG. 5A is a chart which presents the results of an aerosol AATCC 100 killing rate test performed on *S. aureus* using an embodiment of the present invention at 1020 PPM and 3000 PPM chlorine concentrations.
Figure 5B:
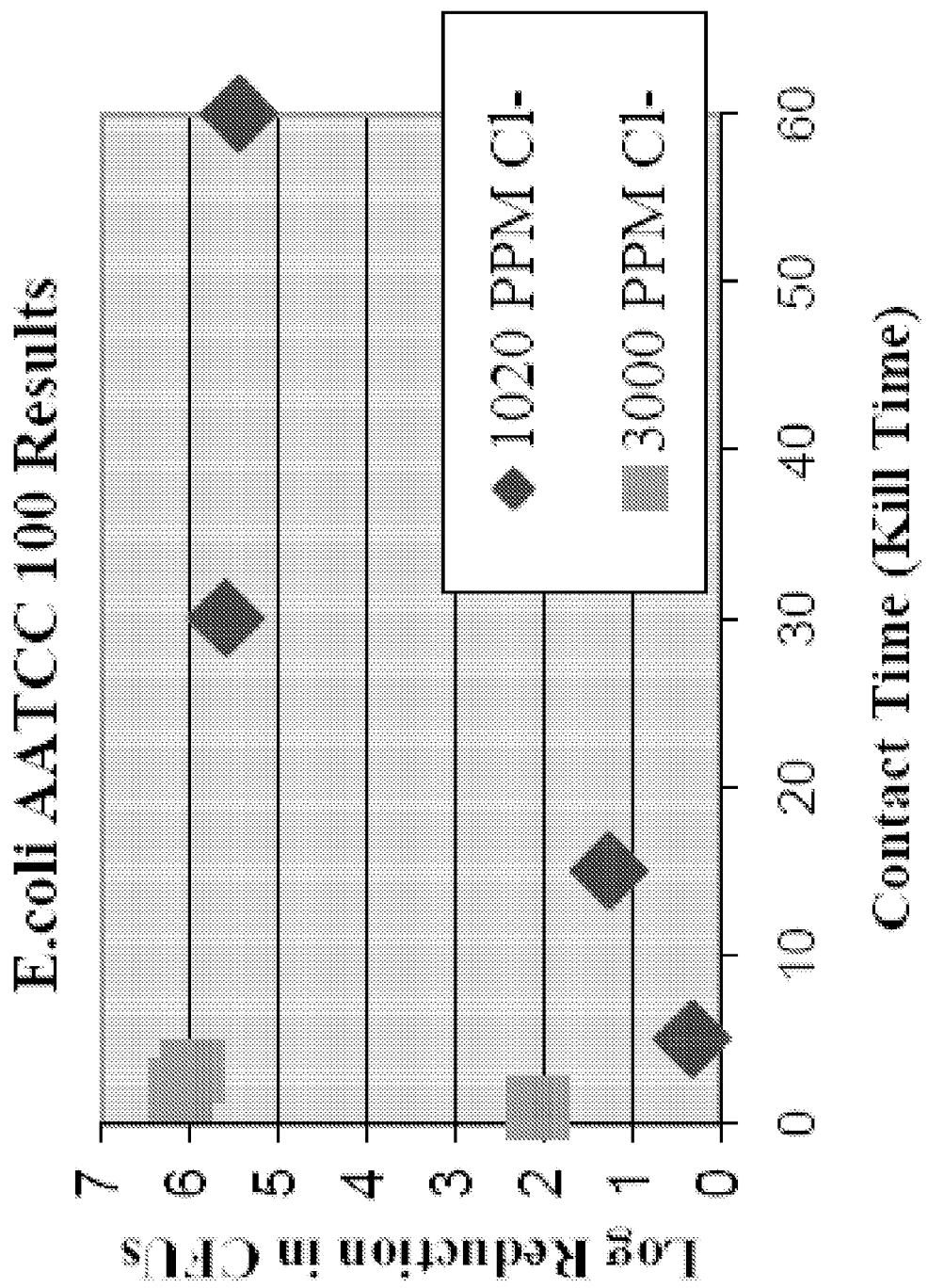
FIG. 5B is a chart which presents the results of an aerosol AATCC 100 killing rate test performed on *E. coli* using an embodiment of the present invention at 1020 PPM and 3000 PPM chlorine concentrations.

FIG. 4 shows *S. aureus* ATCC strain #6538 results from an aerosol AATCC Method 100 assessment of antibacterial finishes on textile materials, with extracted and plated controls on the left 400, 402, 408, 410 and extracted then plated results of chloramine charged textile on the right 404, 408, 412, 414. Five minute results show 0.72-log reduction 404, 406, and 15 minutes result show 6.5-log reduction 412, 414. Cotton textiles in this evaluation had titrated free chlorine at 3000 ppm. FIG. 5A is a chart which presents the results of an aerosol AATCC 100 killing rate test performed on *S. aureus* using an embodiment of the present invention at 1020 PPM and 3000 PPM chlorine concentrations, and FIG. 5B is a chart which presents the results of an aerosol AATCC 100 killing rate test performed on *E. coli* using an embodiment of the present invention at 1020 PPM and 3000 PPM chlorine concentrations.

The original work on siloxane/hydantoin/chloramine chemistry was performed at Auburn University by S. D. Worley et al. The advantage of the hydantoin material is that the silane/siloxane attaching mechanism is a familiar and effective chemistry for fiber and textiles. The halogen discharge process is at the hydantoin end of the structure, with liberation of the bound chloramine to free halogen. Recharging of the chloramine or other halamine on the surface of the fabric is accomplished by subjecting the fabric to a standard wash cycle which includes about 200 ppm of sodium hypochlorite bleach. Siloxane/hydantoin functional groups are not lost from the surface of the fabric during the washing cycle. Therefore, the halogen charge density remains consistent after many recharge cycles.

The fabric of the present invention includes a highly functionalized textile surface which in certain embodiments delivers on the order of 6,000 ppm of titratable free halogen, and in some embodiments delivers 10,000 ppm of titratable free halogen.

Figure 6:
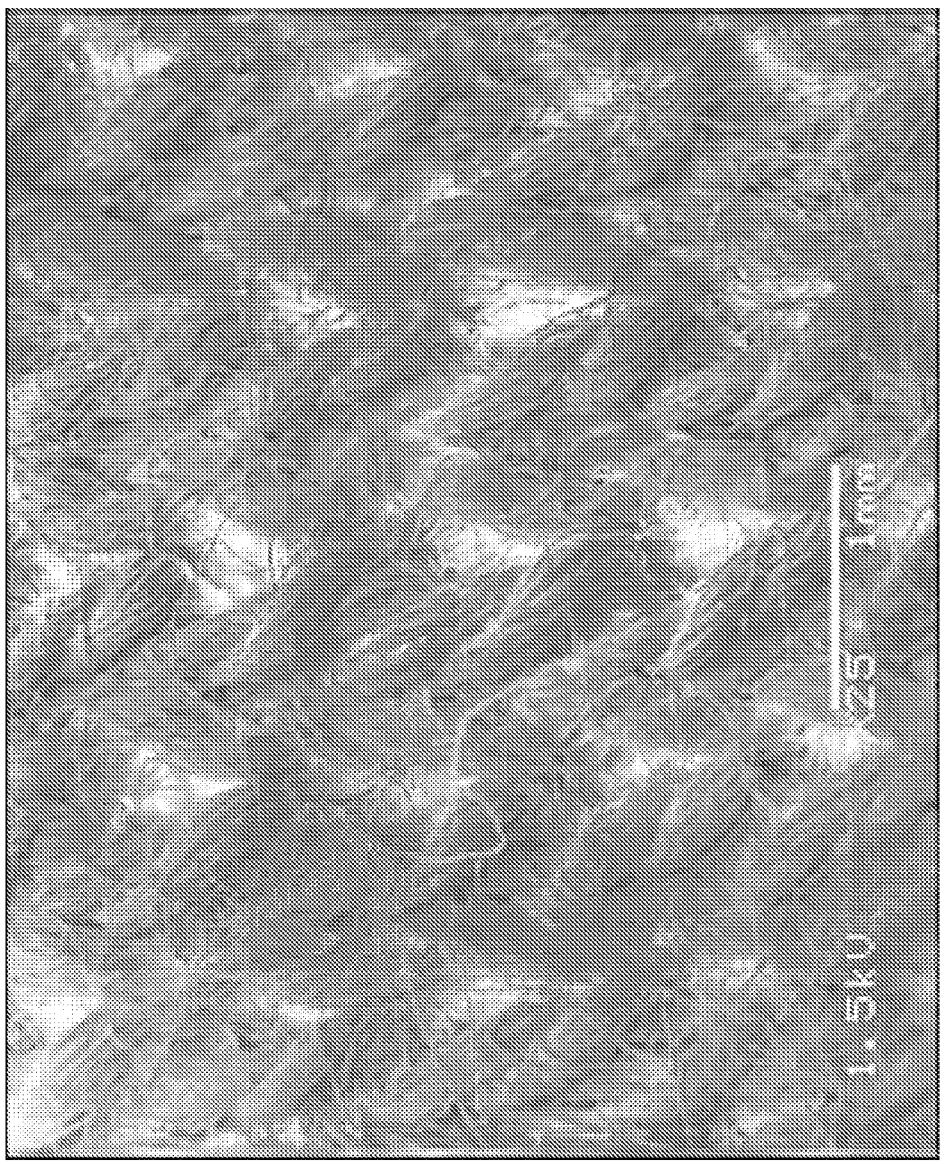
FIG. 6 shows high twist multiple 60/2 pima cotton knit which has been siloxane-hydantoin coated and charged to 6000 ppm of chloramine.

In some embodiments, the fabric includes cotton fiber, which is very compatible with siloxane attachment because of the hydroxylated surface of cellulose. In some of these embodiments, the fabric includes a 2-ply, 80 denier (60/2 cc) warp yarn in combed pima cotton. FIG. 6 shows a high twist multiple 60/2 pima cotton knit which has been siloxane-hydantoin coated and charged to 6000 ppm of chloramine.

Other embodiments include a low twist multiple 80 denier (60/1 cc) yarn, and some of these embodiments include crimp-balanced weaves which achieve high surface planarity and provide interstitial space, which improves the biocidal consistency of the fabric by limiting the entrapment of large soil particles, and improves the skin contact area and thereby improves skin decontamination of the wearer in certain embodiments.

Scouring Process for Hydroxyl Functionality

Figure 7:
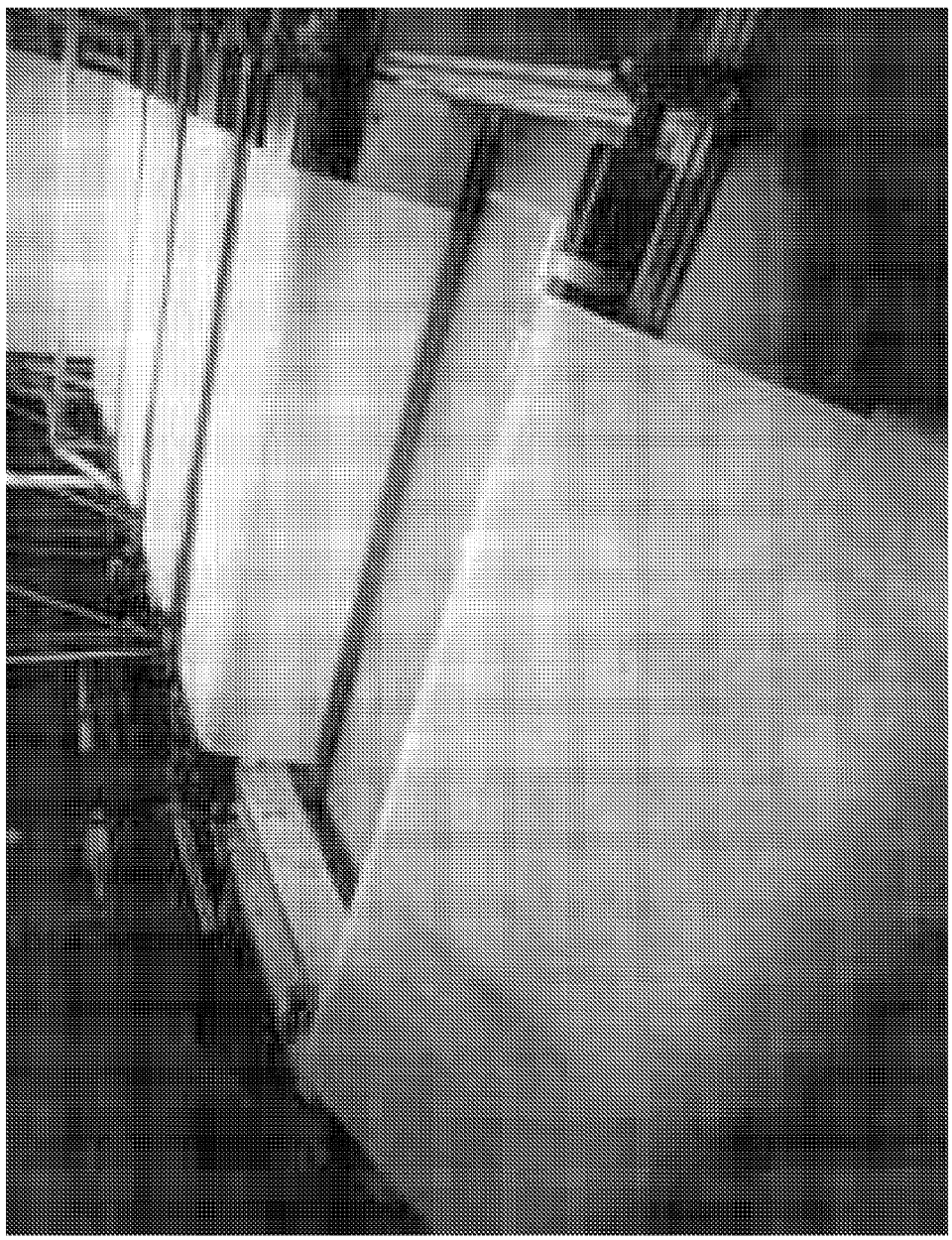
FIG. 7 is a photograph of a scouring process being applied during manufacture of an embodiment of the present invention.

There is a set of natural contaminates and processing aids that are on the surface of all fiber, especially cotton fiber. These oils, waxes and other materials coat the surface of the fiber and impede the siloxane attachment and resultant chloramine density. The performance of the present invention is improved in various embodiments by removal of these contaminates before attachment of the siloxane. The generalized term in textiles for preparation of a fiber surface for application of a dye or coating is "scouring." FIG. 7 illustrates application of a scouring process to fabric during manufacture of an embodiment of the present invention.

In various embodiments which include cotton fiber, a "normal" cotton scour chemistry is used for cotton wax and spin finish removal. Certain embodiments also include a multi-stage fiber surface preparation process which is applied after a series of "normal" scour process steps. In some of these embodiments, the multi-stage process includes use of cellulase enzyme chemistry to improve OH surface functionality. The resultant fabric is as nearly chemically clean as possible in preparation for the siloxane/hydantoin coating stage of the process. The overall goal of this processing is to create the highest possible level of accessible OH functionality on the fiber surface Moisture and Halamine In some embodiments of the present invention the hydration mechanism is adsorption of water on a well-prepared fabric surface, which in certain embodiments is cotton fiber. These embodiments provide the advantages of low cost and complexity of the coating system, since they provide both high levels of siloxane attachment and stoichiometric quantities of retained moisture on the surface of the fabric.

Significantly better kill rates are achieved under moist conditions or high humidity with a basic coating processes. For example, see the work of A. Prugh and J. J. Calomiris, who showed that hydantoin-chloramine's antiseptic performance on a surface is dependent on the availability of moisture.

Figure 8:
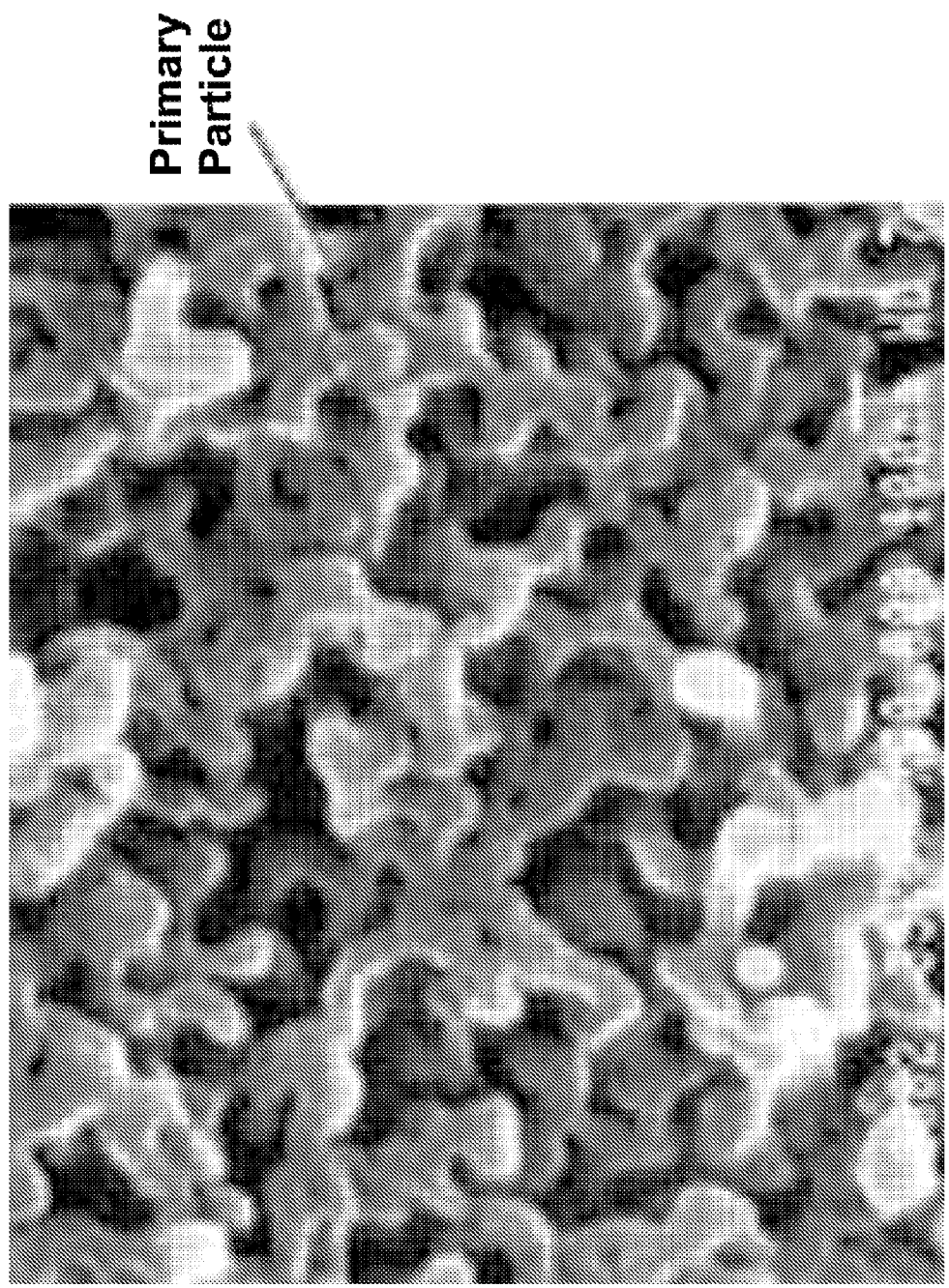
FIG. 8 shows the structure of W.R. Grace silica gel.

For certain embodiments intended for use in ambient conditions of low relative humidity, or under any conditions where increased water is required, a silica gel material is applied at least to the outer surface of the fabric to increase both its surface area and the available moisture. In various embodiments, the silica gel is attached with cellulose acetate resin so as to maintain the overall high level of OH surface functionally of the fabric. And in some of these embodiments cross-linking strategies are used to improve the wash-durability of the cellulose resin. FIG. 8 illustrates the structure of a W. R. Grace silica gel.

Some embodiments provide a siloxane/hydantoin layer on the skin-side of the fabric, thereby forming a halamine layer on the skin side and providing a glove or other garment which provides decontamination of the wearer as well as inhibiting cross-contamination of others. In some of these embodiments where there is direct skin contact with an inner halamine layer, the required moisture is provided to the halamine by perspiration.

Coating With Siloxane/Hydantoin

Figure 9:
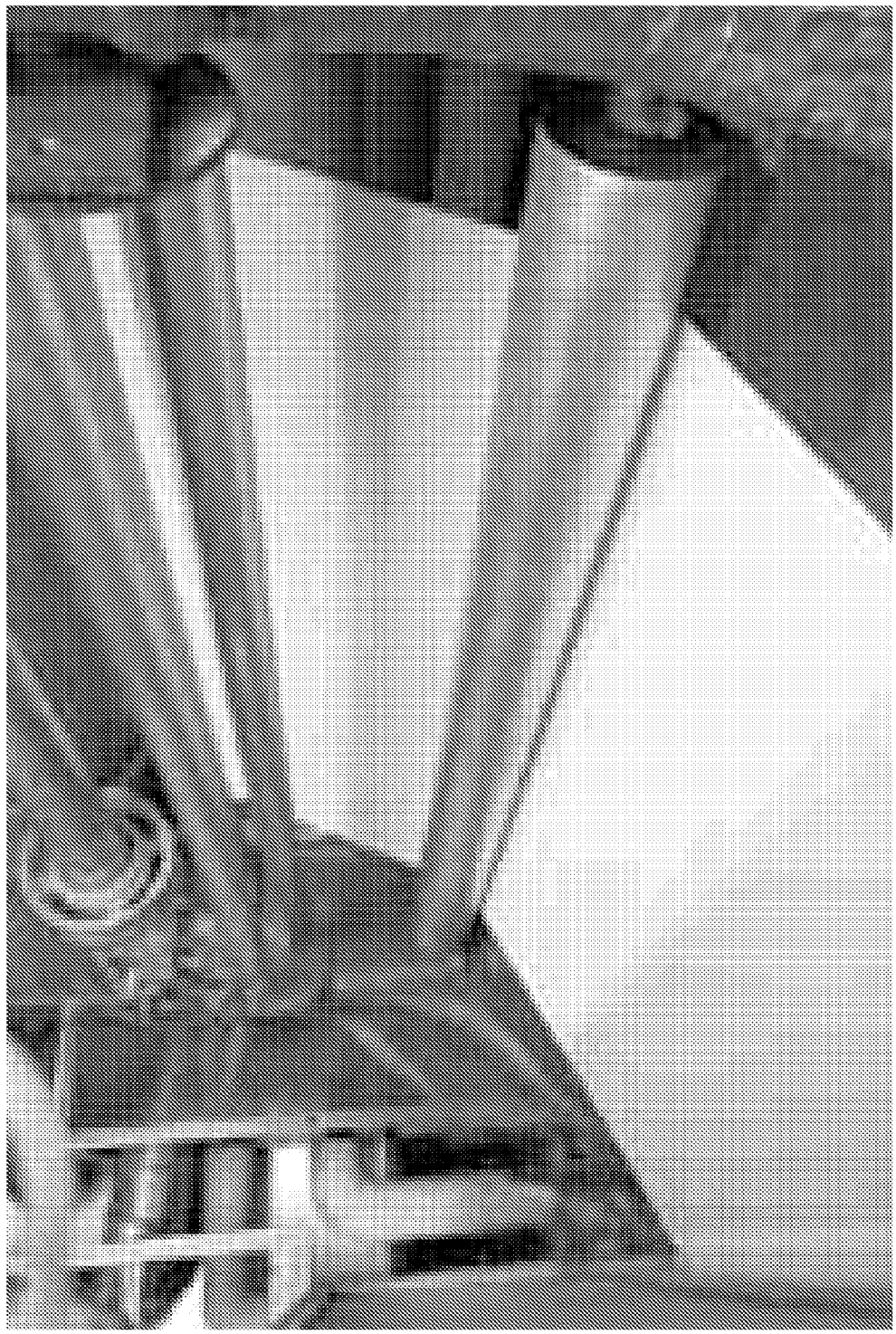
FIG. 9 is a photograph of an ethanol-based hydantoin coating formulation being applied during manufacture of an embodiment of the present invention.

In some embodiments, the siloxane/hydantoin coating is applied after a partial or complete garment article has been formed from the fabric. The article is saturated with siloxane/hydantoin dissolved in an alcohol solvent, and then the article is centrifuged to remove excess coating, with a final step of hot air tumble drying to flash off the alcohol solvent. Because this is a batch-manufacturing process, it is attractive for easy scale-up. Other embodiments use a continuous roll-to-roll process which applies dip, extract, and flash in-line steps to the fabric. This process is illustrated in FIG. 9.

Tests performed by the inventors have shown that increased halamine density is not the only limiting factor in the kinetics of endospore pathogen control. There can be at least 2 additional factors. First is the interfacial compatibility for intimate contact between the pathogen and the fiber surface, and second is the average available free-halogen level.

In embodiments, the fabric of the present invention is engineered to have a very high surface area, so as to enable a high density of chloramine and/or other halamine attachment, and a high degree of interfacial compatibility for intimate contact between pathogens and the fiber surface.

Embodiments of the present invention include forms of chloramine and/or other halamine compounds bonded to the surface of the fabric which provide concentrations of free halogen. Halamine resulting from chlorination of amide forms of hydantoin is used in some embodiments to provide free halogen concentrations of up to 1-2 ppm, while also providing long usage times between halogen recharges. Using the methods in the FDA Tentative Final Monograph for extraction of average available chlorine, it can be shown that the amide form of hydantoin used for chloramine-attachment limits the average available free chlorine to less than 2 ppm at the textile surface.

In other embodiments, halamine formed from an imide form of hydantoin such as 1,3-dimethylol-5 5-dimethylhydantoin (also referred to herein as "DMDMH") is used, either alone or in combination with amide and/or other forms of hydantoin. Imide forms of hydantoin have lower binding energy to halogen ions than amide forms, and can result in up to five times higher levels of free halogen at the textile surface, i.e. up to 10 ppm. Prior to the present invention, imide hydantoin compounds were not used to impart biocidal properties to fabrics, due to their rapid release of halogen and the resulting short usage times between recharging. However, the enhanced fabric surface areas and novel fabric pre-treatments used in embodiments of the present invention enable attached halamine concentrations of up to 6,000 ppm, or even 10,000 ppm, thereby providing usage times of 80 to 400 hours between recharging of the imide hydantoin with halogen.

Pathogen Barrier Layer

Yet another general aspect of the present invention is a pathogen barrier layer, which can be provided either alone or in combination with other physical and/or chloramine layers. In various embodiments, the pathogen barrier layer has high mechanical strength both in tensile and in puncture, even though such pathogen barrier layers have typical area densities of 10-20 g/m$^2$. For some pathogen barrier layers that include membranes made from nano-fibers such as CNT fibers, the nano-fibers are laid in random or semi-random mats. This does not provide for high tensile conversions of the base fiber properties. Even without orientation of the fibers as in a woven material, in certain embodiments the barrier layer provides properties of:

Tensile strength 1 kg/25 mm/20 g of basis weight, where specific tensile strength is calculated by dividing the strength in grams of force per 25 mm strip by the mass-per-square meter in grams:
puncture resistance of 600 gr-5000 gr; and
MVTR greater than 0.2-0.10 mg/cm$^2$/min.

Embodiments use high tenacity nano-fiber materials so as to perform at this level in a random oriented mat. It is believed that the length-to-diameter ratio of the nano-fiber is very important to this mechanical performance. Some embodiments of the present invention include nano-fibers composed of carbon nano-tubes with a length-to-diameter (L/d) ratio in a range of about 1 to 40 million.

In various embodiments, the pathogen barrier layer includes the following strata:
Urethane or CNT membrane layer;
Fiber support layer; and
Second membrane layer (to improve durability and pathogen protection)

The process for manufacture of high strength nano-fiber for some embodiments of the present invention includes the following steps:
Nano-fiber production;
(cleaning steps for some fibers);
Nano-fiber lay-down-mat formation;
(cleaning steps for some fibers);
Coating application to clean unconsolidated mat with control of MVTR; and
Mat consolidation (some embodiments include application of temperature and pressure)

In various embodiments, fibers are combined in layers of plies to create a continuous mat with the capacity to produce water column resistance.

Some nano-fiber production methods result in byproduct contaminates that reside on the fiber surfaces. In some embodiments using carbon nano-tubes ("CNT") and/or aramid pulp, these contaminates are removed before the final consolidation of the barrier mat. In certain of these embodiments, ultra-sonic and solvent methods are used to produce interlayer adhesion in CNT mats. Para-aramid fibrillate typically provides an uncontaminated surface and does not require contaminant removal, since processing organics are not required for the melt film fibrillation process.

In various embodiments, the nano-fiber layers retain sufficient porosity to deliver MVTR of 0.2 mg/cm$^2$/min, which is sufficient for most PPE garments to be comfortable, and some embodiments deliver 0.6 mg/cm$^2$/min. One of the important and novel aspects of some embodiments of this invention is the design of mechanically durable nano-fiber layers, such as CNT layers. In these embodiments, the nano-fiber has high L/d ratio, the lay-down entanglement is high, and the processed mat has enough adhesive coating to prevent interlayer de-lamination, and enough topcoat to prevent abrasion and puncture failure, while preserving these high levels of MVTR.

Protective Layer

Another general aspect of the present invention is a protective layer, which can be provided either alone or in combination with other physical and/or chloramine layers. The protective layer preserves the integrity of any inner layers, if present, and protects a user against a group of threats. The most difficult of these threats are small, sharp hypodermic needles. Needles of approximately 28 gauge are small in diameter and are made of hard steel. Other important threats are tattoo needles and razor knife blades. In general, these threats have sharp cutting edges, and in the worst case are very small in size. The draft ASTM hypodermic needle test protocol can be used to measure 28 gage needle penetration force and the EN 388 cut test protocol can be used to measure shell material cut resistance.

Certain embodiments of the present invention defeat these threats by incorporating a layer of ceramic or cermet grains or platelets on the surface of the protective layer in a dense coating, attached by an adhesive using any of various hot melt and chemical bonding strategies. After attachment of this low porosity layer with MVTR of 0.3 to 0.6 mg/cm$^2$/min, the protective layer is flexed to develop controlled porosity and improve the flexibility of the protective layer.

Figure 10A:
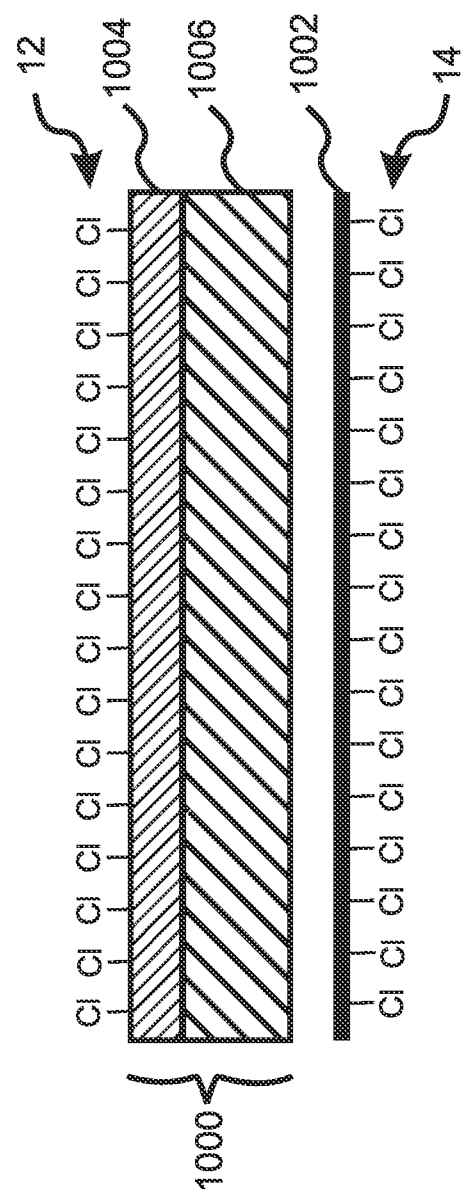
FIG. 10A is a cross-sectional diagram of an embodiment that includes a two-ply protective layer and a pathogen barrier layer, both having layers of halamine applied thereto.

With reference to FIG. 10A, some embodiments of the present invention include a cut-resistant and puncture-resistant protective layer 1000 and a pathogen protecting barrier layer 1002. These two physical layers 1000, 1002 are combined in some embodiments to create a fully protecting personal protection equipment ("PPE") garment, such as protective gloves worn by medical, biohazard, and law enforcement professionals. Both of the physical layers 1000, 1002 in FIG. 10A are mechanically durable and resistant to damage, and in various embodiments both of the layers 1000, 1002 provide high Moisture Vapor Transmission Rates (MVTR).

The protective layer 1000 in the embodiment of FIG. 10A has a hardness greater than Rockwell 40 c and a Moisture Vapor Transport Rate (MVTR) of greater than 0.2 g/cm$^2$/min. It comprises a continuous metal-cermet-ceramic porous layer 1004 bonded to a woven or knit fibrous substrate 1006 such as a para-aramid, for example style 1094 para-aramid. The pathogen barrier layer 1002 includes at least one thin membrane, such as a TCU membrane or a membrane of non-woven carbon nano-fiber (CNT) mat, and can include three or more such membranes bonded to each other. For some embodiments that use a urethane membrane, an additional inner liner is included so as to provide the inner chloramine layer 14, and the inner liner, pathogen barrier layer 1002 and outer shell are separable so as to protect the TCU membrane(s) from degradation during chloramine recharging. In the embodiment of FIG. 1C, the pathogen barrier layer 1002 includes a CNT membrane, and layers of chloramine are applied to both the outer surface 12 of the protective layer 1000 and the inner surface 14 of the pathogen barrier layer 1002. In various embodiments, one or both of these chloramine layers 12, 14, is/are omitted. In some embodiments, only the protective layer 1000 is included, while in other embodiments only the pathogen barrier layer 1002 is included.

Figure 10B:
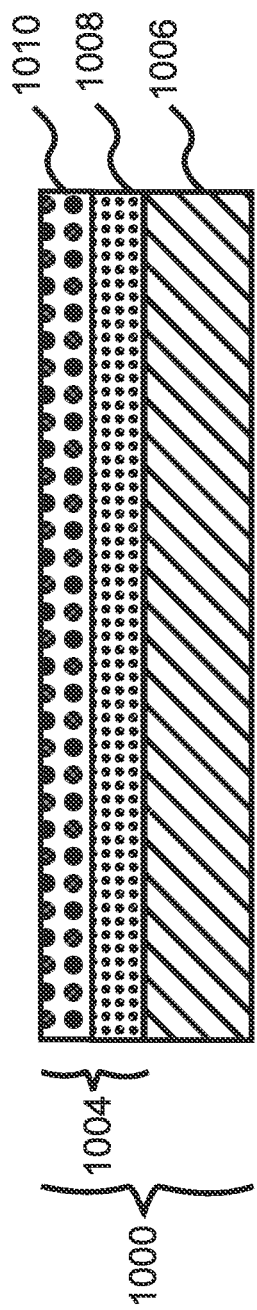
FIG. 10B is a cross-sectional detail of a protective layer in an embodiment wherein the protective layer includes two metallic layers applied to a prepared para-aramid fabric.

FIG. 10B illustrates an embodiment of a protective layer that involves the deposition of molten zinc, copper and/or aluminum droplets 1008 onto the surface of a prepared para-arimid fabric 1006. Similar embodiments use other soft metal coatings, which can be combined successfully with a matching adhesive basecoat.

In some embodiments, this soft metal layer 1008 is applied as a 100% solids spray onto the surface of the fabric 1006. In certain of these embodiments, this soft metal layer 1008 is continuous over the surface. The droplet size, impact velocity, and metal temperature are selected to create this continuous soft metal layer 1008.

In various embodiments a hard-coat layer 1010 is applied on top of the layer of zinc or other soft metal 1008. Tungsten carbide, steel, various cermets, and metal combinations are all useful as hard-coat layers 1010 in various embodiments. These materials have higher melt temperatures than the soft metal layer 1008, and are more difficult to fuse into a continuous layer 1010. The hard material drops form small distorted platelets upon cooling on the fabric surface 1006. The platelets are continuous and interlocking, so as to provide protection from needle penetrations. If the droplet size it too large, the unfused regions between hard particles are points of vulnerability for a needle puncture. Therefore, in various embodiments, a particle size is selected that is much smaller than the diameter of the puncture threat. In the embodiment of FIG. 10B, the particle size is less than 10% of the threat diameter.

In a typical embodiment, the strata that are combined to form the protective layer are as follows:
Web adhesive;
Metal-adhesive primer;
Hard metal layer (Tungsten Carbide for example);
Soft metal adhesive layer (zinc or copper, for example;
Textile surface primer;
Textile support layers (such as 3 oz/yd$^2$ para-aramid style 1094); and
Hydantoin-chloramine layer.

Figure 11:
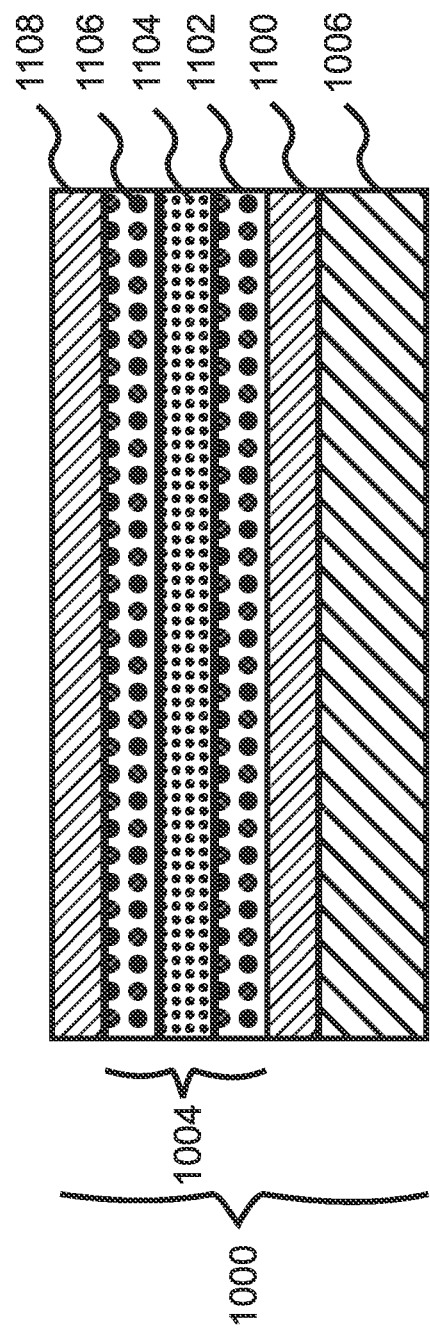
FIG. 11 is a cross-sectional detail of a protective layer in an embodiment wherein the protective layer includes three metallic layers bonded by a single adhesive layer to a para-aramid fabric, the three metallic layers being top-coated by a stabilizing foam layer.

Examples of hard-coat materials include:
Cobalt based: Co 25.5Cr 10.5Ni 7.5W 0.5C;
Carbon steel: Fe 3Al 3Mo 3C0.1B;
Stainless steels: Fe 17Cr 12Ni 2.5Mo 2.3Si 0.1C (AISI Type 316 stainless steel);
Hard Stainless steel: Ni 8.5Cr 7Al 5Mo 2Si 2B 2Fe 3TiO;
Hard Chrome steel: Fe 18Mo 3C 0.25Mn;
Nickel based Hard-coat: Ni 9.5Cr 2.5Si 1.5B 0.5Al;
Cermet Hard-coat: Al2O3 30(Ni 20Al);
Chrome-Carbide Hard-coat: Cr3C2 7(Ni 20Cr) Self-Fusing Nickel Alloy;
Tungsten Carbide cobalt matrix: WC 20Co; and
Aluminum-Titanium Ceramic: Al$_2$O$_3$ 40TiO$_2$ With reference to FIG. 11, in another embodiment an adhesion-primed para-aramid woven substrate 1006 of density 90 g/m$^2$ is coated with 30 g/m$^2$ of a polyether thermoplastic urethane PETPU 1100. The first layer of the metal complex 1102 is 60 g/m$^2$ of zinc applied by wire feed thermal spray. Fine particulate tungsten carbide in a cobalt matrix is then applied 1104 at 100 g/m2 by combustion thermal spray powder feed. This hard-coat metal complex is finished with a nickel-based hard spray 1106 applied at 60 g/m$^2$, also powder fed to a combustion thermal spray process. The metal complex 1004 and top layer of the textile 1006 are saturated with a solution of THF and PETPU at 5% solids with added PAPI at 5% of the solids. The entire protective layer 1000, including the brittle metal complex 1004, is flexed in bending to a radius of 1 mm in both warp and fill, and is sheared under normal load of 10 kg/25 mm at more than 15% shear strain. After post-spray flexing and shearing, the material is top-coated with a stabilized open cell foam 1108 formed from a polycarbonate urethane emulsion with a fine-particle carbon black filler.

Figure 12:
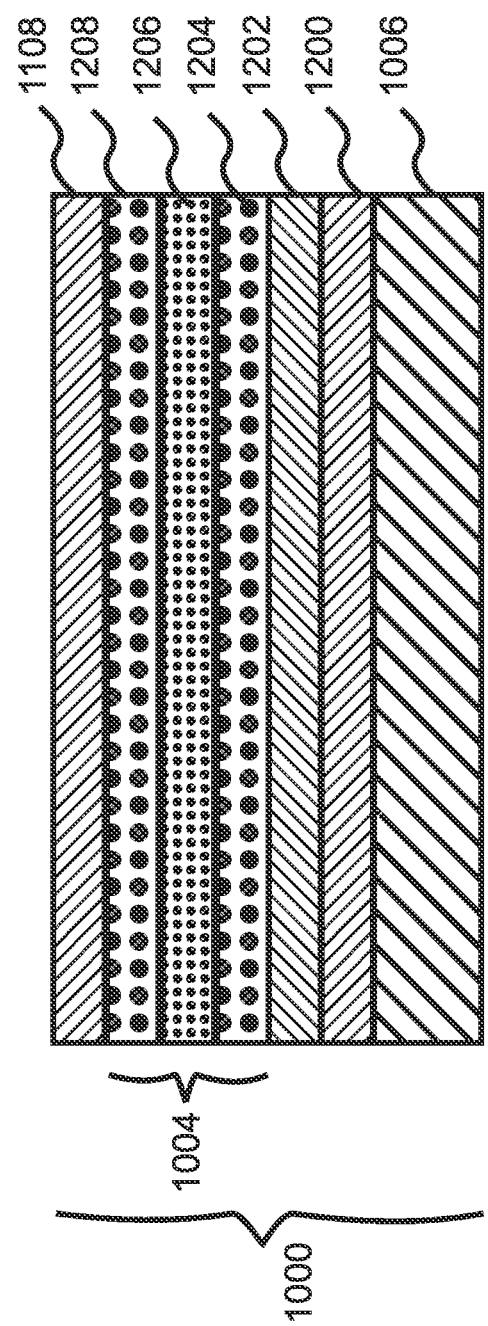
FIG. 12 is a cross-sectional detail of a protective layer in an embodiment wherein the protective layer includes three metallic layers bonded by two adhesive layers to a para-aramid fabric, the three metallic layers being top-coated by a stabilizing foam layer.

With reference to FIG. 12, in yet another embodiment an adhesion-primed para-aramid woven substrate of 30 g/m$^2$ 1006 is coated with 15 g/m$^2$ of para-aramid jet spun fibrillate 1200 and 10 g/m2 of a polyether thermoplastic urethane PETPU 1202. The first layer of the metal complex 1204 is 20 g/m$^2$ of zinc and is applied by wire feed thermal spray. Fine particulate alumina ceramic in a nickel matrix 1206 is applied at 60 g/m$^2$ by combustion thermal spray that is powder fed. This hard-coat metal complex 1206 is finished with a nickel-based hard spray 1208 applied at 30 g/m$^2$, also powder fed to a combustion thermal spray process. The metal complex 1004 and top layer of the textile 1006 are saturated with a solution of THF and PETPU at 5% solids with added PAPI at 5% of the solids. The entire protective layer 1000, including the brittle metal complex 1004, is flexed in bending to a radius of 1 mm in both warp and fill and sheared under a normal load of 10 kg/25 mm at more than 15% shear strain. After post-spray flexing and shearing, the material is top-coated 1108 with a stabilized, open cell foam formed from a polycarbonate urethane emulsion with a fine particle carbon black filler.

Protective Layer MVTR Flex Post Processing

The lack of full fusion of the hard platelets in the protective layer of various embodiments provides for some porosity even at full apparent coverage with small droplet size. The selection of the droplet size and the spray process is governed by the hardness required and the adhesion and durability of the coating. However, in general, a durable hard-coat with good attachment to the fiber substrate, soft metal and other adhesives has unacceptable stiffness and inadequate MVTR.

Therefore, the development of full MVTR in the finished layer requires post-spray processing of the protective layer.

The metal complex layer 1004 as it is originally applied and without flexing is too stiff for use in PPE and has a low MVTR. Even the higher melting temperature, more porous hard-coat materials have high stiffness and limited MVTR in their as-sprayed condition. A novel aspect of the protective layer 100 of the present invention is the use of a post-spray flexing process that forms cracks in the metal strata of the protective layer. The soft metal layer is often selected, as it is self bonding and forms a continuous sheet that is well adhered to the substrate.

In the flexing process the flex fold points of the textile substrate are transferred as fine cracks to the metal complex 104. This flex process is highly effective if the textile flex geometry is patterned in the metal complex layer. In the case of a woven material, this includes a percentage of the warp and fill spacing lines and a percentage of the bias or +/−45 degree lines on the warp and fill spacing. It is obviously critical to some embodiments that this flex process leave an intact continuous metal complex layer 1004. The flexing process can be thought of as the formation of small, bonded, hard regions that permit piece-size flexibility. The flexing process in various embodiments generates minimal metal layer loss during the flexing step. The flex lines generate flexibility in coated substrates without gaps in the cut and puncture protection. These cracks are difficult to see with an optical microscope and are only visible when the substrate is flexed to a sharp angle.

A second novel aspect of the protective layer in some embodiments of the present invention is the use of soft elastomeric coatings and adhesives to permit the flexing of the metal layers 1004 on the fiber substrate 1006. In various embodiments, these coatings are applied before flexing as a saturant to the metal complex layer and the fiber substrate. Adhesive primers suitable for the metal complex can be applied first, with the elastomeric saturant applied second.

The mechanical integrity of metal complex attachment to the substrate 1006 is maintained by well-designed coatings that have elongations of 100-400%. This permits the flex and bias stretch of the base textile, while at the same time retaining the stiff-brittle metal complex on the surface. Polyurethane or neoprene elastomers are coatings with good adhesion to the metal and textile and high elongation.

Thermoplastic Polyether Urethanes-PAPI Mixtures

Saturants 1202 include neopreen elastomers with sulfur cure and PAPI cure and adhesion promoters. The adhesive basecoat 1200 can be of hot-melt adhesive as a preparation of the fabric surface 106 prior to application of the metal droplets 1004. A chemical bond can also be developed with the use of sulfur-cured elastomer adhesives in the base coat 1200. Control of soft metal and hard-coat porosity and adhesion is important in some embodiments to the creation of a durable material with high MVTR performance.

Poor adhesion in the design of the soft metal and hard-coat attachment is manifest in loss of small flakes of hard-coat layer and increased vulnerability of the protective layer to penetration. An additional element of the protective layer 1000 in some embodiments is the use of a cover coat 1108 on top of the hard-coat layer 1004. This is of particular importance if the hard-coat layer 1004 is used as the wear layer in PPE. Foam or other open cell PU coatings 1108 are useful for cover coat applications, and further improve the retention and control of hard-coat elements 1004 while preserving MVTR.

The use of a series of porous hard element layers 1004 with a carefully controlled adhesive process creates a unique, mechanically protective layer that defeats even the smallest needle-like penetrators and preserves a breathable high MVTR.

A hypodermic needle penetration has been used to measure protective layer performance. Peak penetration force with 28 gauge needles of greater than 400 grams is desired for many requirements and values in excess of 800 grams have been found to be useful. The range of penetration values is an excellent measure of the effectiveness of the adhesion system in the hard-coat. In designs with poor adhesion after flex cycling the range of penetration values is increased. Too much adhesive results in low MVTR values.

Combination of Protective Layer and Barrier Layer

As described above with reference to FIG. 10A, some embodiments of the present invention combine a nano-fiber pathogen barrier layer 1002 with a protective layer 1000 which forms the outer face of the system. One of the novel aspects of these embodiments of the present invention is the comparative independence of these two primary layers. In typical prior art approaches the protective layer is intimately attached to a carrier substrate, which provides mechanical protection and support. In these prior art approaches, the pathogen barrier layer is not mechanically competent enough to be used without semi-continuous support.

In various embodiments of the present invention, the pathogen barrier layer 1002 is mechanically competent, and need only be attached to the protective layer 1000 as required by the PPE to maintain alignment and maintain usability of the PPE. For example, in some embodiments the protective layer 1000 is attached to the barrier layer 1002 only at seams of the garment. One of the novel aspects of the present invention therefore is the innovation of a pathogen barrier layer 1002 that is independent of the protective layer 1000, thereby permitting very flexible PPE constructions. In typical prior art configurations, the pathogen barrier layer must be attached to the outer substrate or to an inner liner fabric so as to provide adequate mechanical protection to a mechanically fragile pathogen barrier layer. In embodiments of the present invention, the pathogen barrier layer 1002 can be maintained as a separate layer, greatly improving the comfort of the PPE system. In some embodiments of the present invention, a lightweight inner liner 16 is added, but it need not be adhered to the pathogen barrier layer 1002, which would otherwise increase stiffness.

Another the novel aspect of some embodiments of the present invention is the separation of the hard-coat layer 1004 from the pathogen barrier layer 1002 by the textile 1006 which carries the hard-coat metal complex 1004. Because the pathogen barrier layer 1002 is not continuously attached to the protective layer 1000, the pathogen barrier layer 1002 would be susceptible to abrasion by the hard-coat metal layers 104 if the textile layer 1006 did not act as a separator that permits the loose, flexible protective and pathogen barrier layers 1000 1002 to move relative to each other without risk of damage to the pathogen barrier layer 1002 by the hard-coat layer 1004.

Multiple Combined Layers

Figure 13:
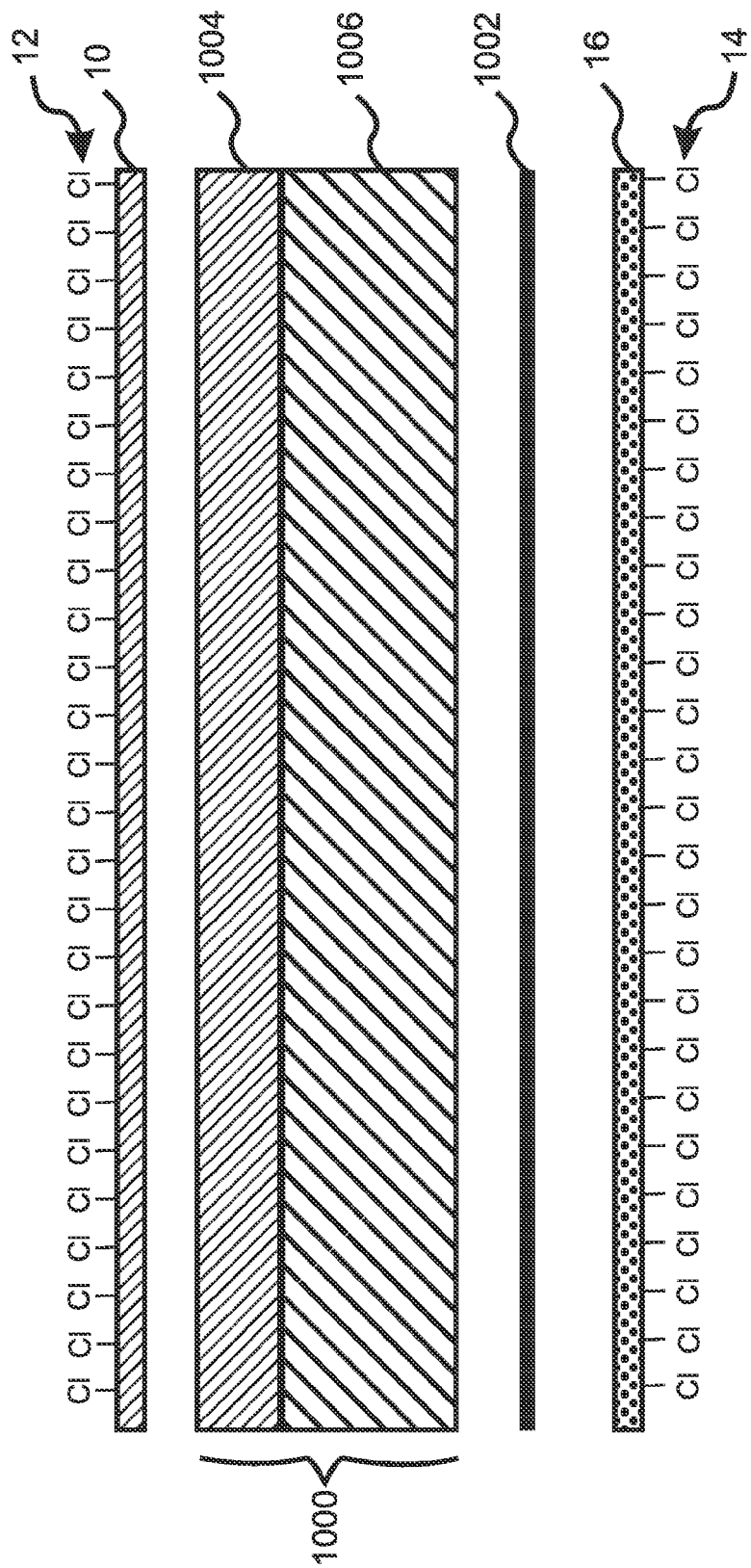
FIG. 13 is a cross-sectional diagram of an embodiment that includes an outer shell, a protective layer, a pathogen barrier layer, and an inner liner, the outermost and innermost surfaces of the embodiment having chloramine layers applied thereto.

With reference to FIG. 13, in some embodiments various physical layers and layers of chloramine as described above are combined within a single embodiment of the present invention. In the embodiment of FIG. 13, the outer surface of the outer shell 10 is coated with a layer of a halamine such as chloramine 12, and is compatible with disinfection by alcohol-based products as discussed above with reference to FIG. 1A. Beneath the outer shell 10, a protective layer 1000 inhibits penetration of the garment by punctures and cuts. Beneath the protective layer 1000, a pathogen barrier layer 1002 provides physical protection against penetration by pathogens. Finally, an inner liner 16 enhances the comfort of the user, and maintains an inner coating of chloramine 14 in contact with the skin of the user so as to eliminate any contamination that may have reached the skin, for example during temporary glove removal for recharging of the chloramine. All of the layers in the embodiment of FIG. 13 provide a Moisture Vapor Transport Rate (MVTR) of greater than 0.2 g/cm$^2$/min.

Figure 14:
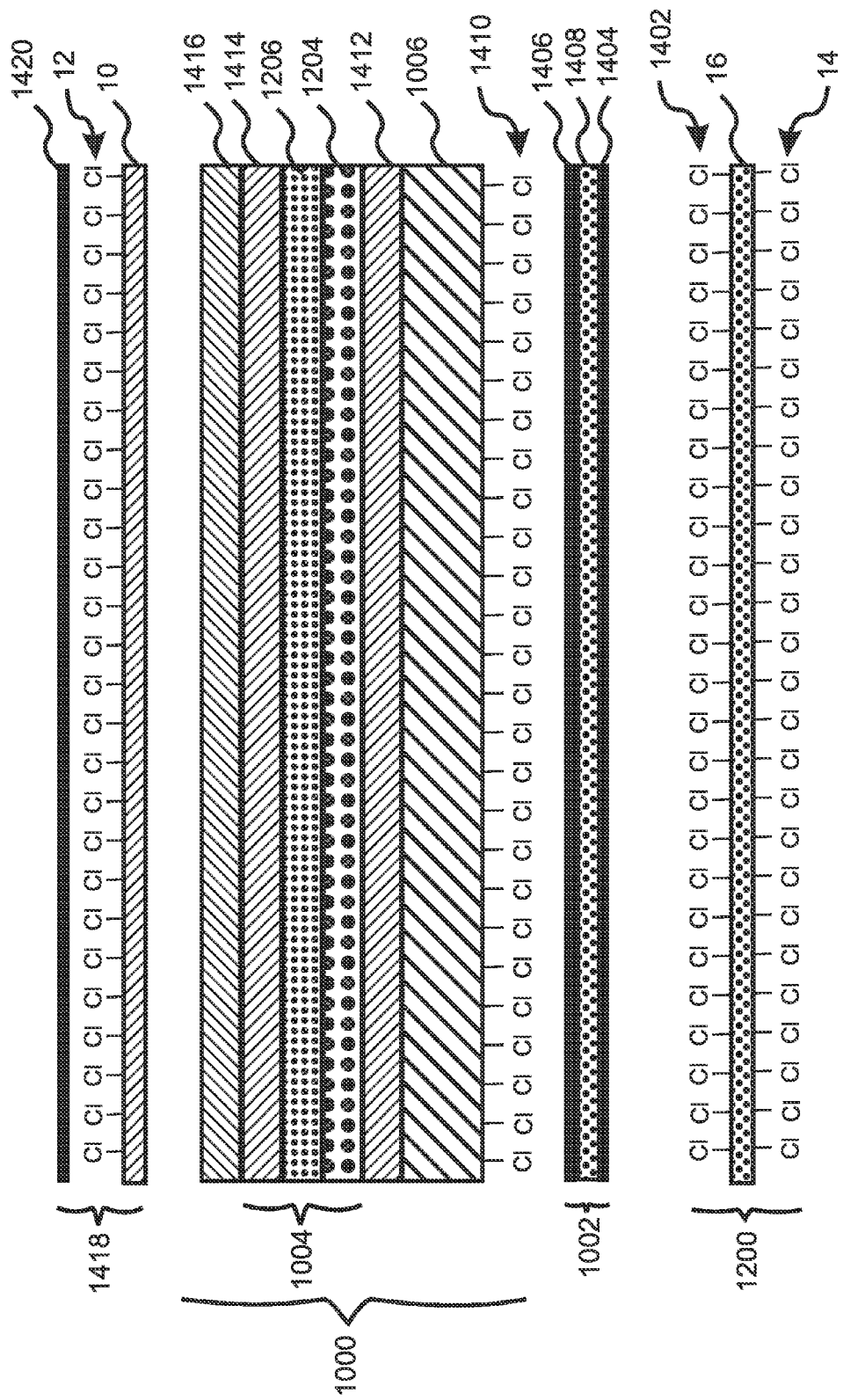
FIG. 14 is a cross-sectional diagram of an embodiment that includes an outer shell, a protective layer, a pathogen barrier layer, and an inner liner, a plurality of the surfaces thereof having chloramine layers applied thereto, and the outermost surface having a durable water-repellant layer applied thereto.

FIG. 14 presents a cross-section of a glove embodiment that combines multiple physical and chloramine layers. An inner liner 1200 is provided that comprises a fine-gauge string-knit glove 16 made from Meta aramid with chlorine resistant PTT or PBT stretch polyester or other chlorine resistant stretch yarn. Both surfaces of the inner liner 1200 are coated with Hydantoin-chloramine layers 14, 1402. The inner liner 1200 is tight fitting to the hand and fingers of a user, so as to maintain intimate contact of the inner chloramine layer 14 with the skin of the user's hand.

A pathogen barrier layer 1002 overlays the inner liner 1200, and comprises a pair of either urethane or CNT membranes 1404, 1406, sandwiched on either side of a fiber support layer 1408. For some embodiments, especially embodiments where at least one of the membranes is urethane, the pathogen barrier 1002 is separable from the other layers for chloramines recharge, since urethane membranes are not resistant to chlorine solutions.

The inner liner 1200 and pathogen barrier 1002 layer are protected from punctures and cuts by a protective layer 1000. The protective layer 1000 includes a textile support layer 1006 comprising at least one layer of woven 3 oz/yd$^2$ high density LCP Vectran. The textile support layer 1006 includes a layer of chloramine 1410 on its inward-facing surface, and is topped by a textile surface primer 1412 onto which are deposited a zinc metal adhesive layer 1204 and a hard metal layer 1206 comprising a hard metal such as tungsten carbide. The hard metal layer 1206 is topped by a metal-adhesive layer 1414 and finally a web adhesive 1416.

The protective layer 1000 is covered by an outer layer 1418 that includes a controlled-porosity outer shell 10. The palm and fingers of the outer shell 10 comprise synthetic suede or full grain glove leather, while the back of the outer shell 10 comprises meta-aramid combined with LCP and chlorine resistant PTT or PBT stretch polyester. The outer shell 10 is compatible with ethanol and propanol sterilization materials such as gels, foams, and rinses. The outward-facing surfaces of the outer shell 10 are coated with hydantoin-chloramine layers 12, and are further coated with a Durable Water Repellant (DWR) 1420.

The foregoing description of the embodiments of the invention has been presented for the purposes of illustration and description. It is not intended to be exhaustive, or to limit the invention to the precise form disclosed. Many modifications and variations are possible in light of this disclosure. It is intended that the scope of the invention be limited not by this detailed description, but rather by the claims appended hereto.

What is claimed is:

1. A self-decontaminating fabric suitable for manufacture of a garment that is wearable by a wearer so as to inhibit cross-contamination of pathogens between individuals with whom the wearer comes in contact, the self-decontaminating fabric comprising:
   a fabric having a first surface and a second surface;
   a layer of N-Cyclic material attached to the first surface, said N-Cyclic material comprising N-Cyclic molecules having a chemical formula that does not include silicon, wherein said attachment does not include covalent bonding of the N-Cyclic molecules to the first surface, the layer of N-Cyclic material being chargeable with a halogen to form a layer of halamine, the layer of halamine being of sufficient concentration to provide to the fabric a maximum 180 second 3-log kill rate, when the halamine layer is moistened with water, for at least *S. aureus* ATCC strain #6538 and *E. coli*, as determined by an aerosol AATCC Method 100 assessment; and
   a hydrating mechanism adapted for said moistening the halamine layer with water.

2. The self-decontaminating fabric of claim 1, wherein at least some of the N-Cyclic molecules are attached by Van der Waals forces to hydroxyl groups of cellulose included in the first surface.

3. The self-decontaminating fabric of claim 1, wherein the halamine layer is able to deliver at least 4,000 ppm of titratable free halogen.

4. The self-decontaminating fabric of claim 1, wherein the fabric contains cotton fiber.

5. The self-decontaminating fabric of claim 1, wherein the fabric contains yarns of less than 200 denier (25 s cc), said yarns being formed from cellulosic fibers.

6. The self-decontaminating fabric of claim 1, wherein the fabric contains a low-twist 80 denier (60/1 cc) yarn.

7. The self-decontaminating fabric of claim 6, wherein the fabric further includes crimp-balanced construction.

8. The self-decontaminating fabric of claim 1, wherein the hydrating mechanism includes an affinity for adsorption of water on the first surface of the fabric that is sufficient to provide said moistening.

9. The self-decontaminating fabric of claim 1, wherein the hydrating mechanism includes a moisture management coating applied to the first surface, the moisture management coating including silica gel.

10. The self-decontaminating fabric of claim 9, wherein the silica gel is attached to the fabric by a cellulose acetate resin.

11. The self-decontaminating fabric of claim 10, wherein the cellulose acetate resin includes Van der Waals attachment which improves its wash-durability.

12. The self-decontaminating fabric of claim 1, further comprising a second layer of N-Cyclic material attached to the second surface, said N-cyclic material of said second layer comprising N-Cyclic molecules having a chemical formula that does not include silicon, said second layer being chargeable with a halogen to form a layer of halamine, wherein said attachment to said second surface does not include covalent bonding of the N-Cyclic molecules to the second surface.

13. The self-decontaminating fabric of claim 1, wherein the N-Cyclic material is chloramine.

14. The self-decontaminating fabric of claim 1, wherein the halamine is an amide halamine.

15. The self-decontaminating fabric of claim 1, wherein the halamine is an imide halamine.

16. The self-decontaminating fabric of claim 15, wherein the imide halamine is 1,3-dimethylol-5,5-dimethyl hydantoin.

17. The self-decontaminating fabric of claim 1, wherein after charging with a halogen the fabric is able to provide the 180 second 3-log kill rate during a period of use of at least 80 hours.

18. The self-decontaminating fabric of claim 17, wherein after charging with halogen the fabric is able to provide the 180 second 3-log kill rate during a period of use of at least 400 hours.

19. A method of producing a self-decontaminating fabric, the method comprising:
   providing a fabric;
   scouring at least a first surface of the fabric and thereby removing surface contaminates;
   attaching a layer of N-Cyclic molecules to the first surface of the fabric, said N-Cyclic molecules having a chemical formula that does not include silicon, whereby said attachment does not include covalent bonding of the N-Cyclic molecules to the first surface, the layer of N-Cyclic molecules being chargeable with a halogen to form a layer of halamine, the layer of halamine being of sufficient concentration, when it is moistened, to provide a maximum 180 second 3-log kill rate for at least *S.aureus* ATCC strain #6538 and *E.coli*, as determined by an aerosol AATCC Method 100 assessment;
   providing a hydrating mechanism adapted for moistening the halamine layer; and
   moistening the halamine layer using the hydrating mechanism.

20. The method of claim 19, wherein scouring at least a first surface of the fabric includes scouring the first surface using a multi-stage process which employs cellulase enzyme chemistry.

21. The method of claim 19, wherein attaching a layer of N-Cyclic molecules to the first surface includes:
   forming at least a partially complete garment incorporating the fabric;
   saturating the garment with N-Cyclic molecules dissolved in a solvent;
   removing excess coating from the garment by centrifuging the garment; and
   flashing the solvent off of the garment by hot air tumble-drying the garment.

22. The method of claim 19, wherein attaching a layer of N-Cyclic molecules to the first surface includes using a continuous roll-to-roll process which applies dip, extract, and flash in-line steps to the fabric.

23. The method of claim 19, wherein the N-Cyclic layer is able to deliver at least 4,000 ppm of titratable free halogen.

24. The method of claim 19, wherein providing a hydrating mechanism includes applying a moisture management coating to the first surface, the moisture management coating including silica gel which is attached to the fabric using a cellulose acetate resin, the cellulose acetate resin being attached to the fabric by Van der Waals forces that improve the wash-durability of the attachment.

* * * * *